(12) United States Patent
Itov et al.

(10) Patent No.: US 8,846,923 B1
(45) Date of Patent: Sep. 30, 2014

(54) PREPARATION OF 14-HYDROXYCODEINONE SULFATE

(71) Applicant: Cody Laboratories, Inc., Cody, WY (US)

(72) Inventors: Zinovy Itov, Cody, WY (US); Vladimir F. Kuznetsov, Cody, WY (US); Iouri Voitsekhovski, Cody, WY (US)

(73) Assignee: Cody Laboratories, Inc., Cody, WY (US)

( * ) Notice: Subject to any disclaimer, the term of this patent is extended or adjusted under 35 U.S.C. 154(b) by 0 days.

(21) Appl. No.: 14/132,825

(22) Filed: Dec. 18, 2013

(51) Int. Cl.
    *C07D 471/00* (2006.01)
    *C07D 489/08* (2006.01)

(52) U.S. Cl.
    CPC .................... *C07D 489/08* (2013.01)
    USPC .......................................... 546/45

(58) Field of Classification Search
    USPC .......................................... 546/45
    See application file for complete search history.

(56) References Cited

U.S. PATENT DOCUMENTS

| | | | |
|---|---|---|---|
| 4,613,668 A | 9/1986 | Rice | |
| 4,795,813 A | 1/1989 | Schwartz | |
| 6,090,943 A | 7/2000 | Mudryk et al. | |
| 6,262,266 B1 | 7/2001 | Chiu et al. | |
| 6,365,742 B1 | 4/2002 | Mudryk et al. | |
| 6,723,894 B2 | 4/2004 | Fist et al. | |
| 6,864,370 B1 | 3/2005 | Lin et al. | |
| 7,071,336 B2 * | 7/2006 | Francis et al. | 546/45 |
| 7,129,248 B2 | 10/2006 | Chapman et al. | |
| 7,153,966 B2 | 12/2006 | Casner et al. | |
| 7,399,488 B2 | 7/2008 | Hirsh et al. | |
| 7,619,087 B2 | 11/2009 | Snuparek et al. | |
| 7,674,798 B2 | 3/2010 | Chapman et al. | |
| 7,674,800 B2 | 3/2010 | Chapman et al. | |
| 7,683,072 B2 | 3/2010 | Chapman et al. | |
| 7,906,647 B2 | 3/2011 | Cox et al. | |
| 7,928,234 B2 | 4/2011 | Carroll et al. | |
| 8,058,439 B2 | 11/2011 | Cox et al. | |
| 8,067,596 B2 | 11/2011 | Wang et al. | |
| 8,067,597 B2 | 11/2011 | Wang et al. | |
| 2005/0222188 A1 | 10/2005 | Chapman et al. | |
| 2007/0179169 A1 | 8/2007 | Chapman et al. | |
| 2008/0139814 A1 | 6/2008 | Cox et al. | |
| 2009/0005563 A1 | 1/2009 | Carroll et al. | |
| 2009/0156820 A1 | 6/2009 | Wang et al. | |
| 2010/0048905 A1 | 2/2010 | Wang et al. | |
| 2010/0152449 A1 | 6/2010 | Chapman et al. | |
| 2011/0136849 A1 | 6/2011 | Shafer et al. | |
| 2011/0144340 A1 | 6/2011 | Cox et al. | |
| 2011/0207762 A1 | 8/2011 | Chapman et al. | |
| 2012/0259118 A1 | 10/2012 | Keskeny et al. | |
| 2013/0005977 A1 | 1/2013 | Chapman et al. | |
| 2013/0035489 A1 | 2/2013 | Weber et al. | |

FOREIGN PATENT DOCUMENTS

| | | |
|---|---|---|
| EP | 2121698 B1 | 2/2012 |
| GB | 939287 A | 10/1963 |
| IN | 1804/DEL/2008 | 4/2010 |
| IN | 2909/MUM/2009 | 7/2010 |
| WO | 2005097801 A1 | 10/2005 |
| WO | 2008070658 A1 | 6/2008 |
| WO | 2008130553 A1 | 10/2008 |
| WO | 2009003271 A1 | 1/2009 |
| WO | 2009004491 A2 | 1/2009 |
| WO | 2011117172 A1 | 9/2011 |
| WO | 2012003468 A1 | 1/2012 |
| WO | 2014/013311 A1 | 1/2014 |

OTHER PUBLICATIONS

Zhang et al. J. Am. Chem. Soc. 2005, 127, 7286-7287.*
Currie et al., "Some Reactions of 14-Hydroxycodeine", Journal of the Chemical Society, Part I(157):773-781 (1960).
Das Sharma et al., "A Simple and Practical Method for the Oxidation of Thebaine to 14-Hydroxycodeinone by V2O5-H2O2", Synthesis, 7:1062-1064 (2008).
Feldmann et al., "Obtaining the Dihydrooxycodeinon Chlorhydrate from Thebaine", Journal of Applied Chemistry (1945) (Russian language with English Abstract).
Gancedo, "Investigaciones sobre una aplicacion del agua oxigenada a la sintesis organica", Anales de la Real Academia de Farmacia, pp. 217-242 (1953). (Spanish language).
Hauser et al., "14-Hydroxycodeinone. An Improved Synthesis", Journal of Medicinal Chemistry 17(10):117 (1974).
Hazard, "Succedanes de la morphine et de la codeine: dilaudide, dicodide, eucodal, acedicone", Journal de Pharmacie et de Chimie, pp. 312-320 (1930). (French language).
Iijima et al., "The Oxidation of Thebaine with m-Chloroperbenzoic Acid. Studies in the (+)-Morphinan Series. III", Helvetica Chimica Acta, 60(7)(213):2134-2137 (1977).
Iijima et al., "Studies in the (+)-Morphinan Series. 5. Synthesis and Biological Properties of (+)-Naloxone", Journal of Medicinal Chemistry, 21(4):398-400 (1978).
Kok et al., "Improved synthesis of 14-hydroxy opioid pharmaceuticals and intermediates", RSC Advances, 2:11318-11325 (2012).
Kraβnig et al., "Optimization of the Synthesis of Oxycodone and 5-Methyloxycodone", Arch. Pharm. Pharm. Med. Chem., 329:325-326 (1996).
Merck, "Wissenschaitliche Mittellungen. Eukodal.", Pharmazeutische Zeitung, 64(38):264 (1919). (German language).
Novak et al., "Morphine Synthesis and Biosynthesis—An Update", Current Organic Chemistry 4(3):343-362 (2000).
Ramanathan et al., "Dihydrocodeine, Dihydrocodeinone, 14-Hydroxydihydrocodeinone & Their Derivatives", Short Communications—Government Opium & Alkaloid Works, Ghazipur 350-351 (1963).
Rapoport et al., "10-Hydroxymorphine", Alkaloids of P. sabiniana Dougl. And Related Species, 77:6359-6361 (1955).
Sasaki et al., "Compounds VI. Transformation of Thebaine to Benzomorphan Analogues by Ozonolysis", Chem. Pharm. Bull, 15(8):1247-1250 (1967).

(Continued)

Primary Examiner — Nizal Chandrakumar
(74) Attorney, Agent, or Firm — Merchant & Gould PC

(57) ABSTRACT

Synthetic methods are provided for preparation of oxycodone and salts thereof with an improved impurity profile. Thebaine is converted to 14-hydroxycodeinone sulfate intermediate to minimize a 7,8-dihydro-8,14-dihydroxycodeinone impurity. Efficient methods for conversion of oxycodone base to oxycodone hydrochloride are provided to minimize 14-hydroxycodeinone impurity in the final product.

10 Claims, 7 Drawing Sheets

(56) References Cited

OTHER PUBLICATIONS

Seki, "An Improved Preparation of 14-Hydroxycodeinone", 14-Hydroxycodeinone, 12:52-55 (1960). (Japanese language with English abstract).

Seki, "Studies on the Morphine Alkaloids and Its Related Compounds. XVII. One-Step Preparations of Enol Ether and Pyrrolidinyl Dienamine of Normorphinone Derivatives", Chem. Pharm. Bull., 18(4):671-676 (1970).

US Pharmacopeial Convention, "Oxycodone Hydrochloride", Revision Bulletin Official pp. 1-3, (Oct. 1, 2010).

Valhari et al., "Synthesis of 6-Methoxymethylmorphinol", Jour. Chem. Soc. Pak., 13(3):169-173 (1991).

Zhang et al., "14-Hydroxylation of Opiates: Catalytic Direct Autoxidation of Codeinone to 14-Hydroxycodeinone", JACS, 127:7286-7287 (2005).

Zhang et al., "14-Hydroxylation of Opiates: Catalytic Direct Autoxidation of Codeinone to 14-Hydroxycodeinone", JACS, 127:S1-S2 (Supporting Information) (2005).

Zhang et al, "The Synthesis of Nalbuphine Hydrochloride", Chemistry & BioEngineering, 24(9):19-21 (2007). (Chinese language) (Chinese language with English abstract).

* cited by examiner

Thebaine

An ABUK Sulfate

An ABUK Sulfate Impure

An ABUK Base (water insoluble)

An ABUK Acetate (water soluble)

An ABUK Sulfate Pure

PREPARATION OF 14-HYDROXYCODEINONE SULFATE

FIELD

Synthetic methods are provided for preparation of 14-hydroxycodeinone sulfate and its use for synthesis of oxycodone and salts thereof with improved impurity profiles.

DESCRIPTION OF THE RELATED ART

Oxycodone hydrochloride is an opioid receptor agonist that is indicated for relief of moderate to severe pain. Preparation of oxycodone hydrochloride from thebaine through intermediate preparation of 14-hydroxycodeinine is a well-known technology that has been employed since 1916.

FIG. 1 shows a prior art conventional synthetic route for preparation of oxycodone hydrochloride by oxidation of thebaine to form 14-hydroxycodeinone (ABUK), reduction of 14-hydroxycodeinone to form oxycodone base, and conversion of the base to oxycodone hydrochloride. A synthetic impurity, 7,8-dihydro-8,14-dihydroxycodeinone, (DHC), interconverts by hydration/dehydration from/to 14-hydroxycodeinone. Conventional conversion methods to form oxycodone HCl from oxycodone base using aqueous HCl at elevated temperatures (40-100° C.), or under reflux conditions, can cause acid catalyzed dehydration of residual DHC impurity to form undesirable ABUK in the final product.

However, the FDA purity requirements for oxycodone hydrochloride have been increased, requiring 14-hydroxycodeinine levels to be less than 10 ppm or 0.001% in the final product. Improved synthetic methodology to provide oxycodone hydrochloride of sufficient purity is desirable.

SUMMARY

Synthetic methods are provided for preparation of oxycodone hydrochloride with an improved impurity profile. Thebaine is converted to 14-hydroxycodeinone sulfate intermediate to minimize a 7,8-dihydro-8,14-dihydroxycodeinone impurity. Efficient methods for conversion of oxycodone base to oxycodone hydrochloride are provided to minimize 14-hydroxycodeinone impurity in the final product.

In some embodiments, a method is provided for preparation of oxycodone comprising exposing thebaine to hydrogen peroxide or peroxyacid and another organic acid in the presence of sodium hydrogen sulfate, sodium sulfate, potassium sulfate, potassium hydrogen sulfate and/or sulfuric acid in an aqueous reaction mixture to form 14-hydroxycodeinone sulfate; reducing the 14-hydroxycodeinone sulfate in the presence of a catalyst to form oxycodone base; and dissolving the oxycodone base in an aqueous organic acid to form an oxycodone organic acid salt. In some embodiments, the oxycodone organic acid salt is converted to oxycodone hydrochloride by adding hydrochloric acid or ammonium chloride to the oxycodone organic acid salt to form oxycodone hydrochloride. In some embodiments, the sodium hydrogen sulfate, sodium sulfate, potassium sulfate and/or potassium hydrogen sulfate is added to the aqueous reaction mixture prior to addition of the hydrogen peroxide or peroxyacid. In some embodiments, the another organic acid is formic acid. In some embodiments, the oxycodone organic acid salt is oxycodone acetate.

In some embodiments, a method is provided for preparing oxycodone comprising exposing thebaine to hydrogen peroxide or peroxyacid and another organic acid in the presence of sodium hydrogen sulfate, sodium sulfate, potassium sulfate, potassium hydrogen sulfate and/or sulfuric acid in an aqueous reaction mixture to form 14-hydroxycodeinone sulfate; reducing the 14-hydroxycodeinone sulfate in the presence of a catalyst to form oxycodone base; and dissolving the oxycodone base in an aqueous organic acid to form an oxycodone organic acid salt. In some embodiments, the method further comprises adding hydrochloric acid or ammonium chloride to the oxycodone organic acid salt to form oxycodone hydrochloride, wherein any 8,14-dihydroxy-7,8-dihydrocodeinone impurity present in the oxycodone base is not converted to 14-hydroxycodeinone.

In some embodiments, a method is provided for preparation of oxycodone hydrochloride comprising oxidizing thebaine to provide 14-hydroxycodeinone sulfate and further comprising isolating the 14-hydroxycodeinone sulfate from the aqueous reaction mixture to form isolated 14-hydroxycodeinone sulfate or a hydrate thereof. In some embodiments, the 14-hydroxycodeinone sulfate hydrate is selected from a hemihydrate, monohydrate, sesquihydrate, or dihydrate.

In some embodiments, a method is provided for providing oxycodone hydrochloride comprising reducing the isolated 14-hydroxycodeinone sulfate or a hydrate thereof in the presence of the catalyst to form oxycodone base. In some embodiments, the oxycodone base is purified to form purified oxycodone base. In some embodiments, the purified oxycodone base has not more than 0.10%, 0.05%, or 0.01% of a 8,14-dihydroxy-7,8-dihydrocodeinone (DHC, DHDHC) impurity.

In some embodiments, a method is provided for converting oxycodone base to oxycodone hydrochloride comprising dissolving oxycodone base in an aqueous organic acid. In some embodiments, the dissolving comprises complete or partial dissolution of the oxycodone base in the aqueous organic acid. In some embodiments, the aqueous organic acid is aqueous acetic acid. In some embodiments, the dissolving step is performed at a temperature within the range from about 0° C. to about 70° C.; about 0° C. to about 60° C.; about 0° C. to about 50° C.; or about 10° C. to 40° C.; or at ambient temperature. In some embodiments, the purified oxycodone hydrochloride has not more than 0.15%, 0.10%, 0.05%, or 0.01% of an 8,14-dihydroxy-7,8-dihydrocodeinone (DHC) impurity.

In some embodiments, methods comprise purifying the oxycodone hydrochloride by a method comprising crystallizing the oxycodone hydrochloride to form purified oxycodone hydrochloride. In some embodiments, the crystallizing is performed by addition of water and/or one or more water miscible organic solvents to the oxycodone hydrochloride to form the purified oxycodone hydrochloride. In some embodiments, the crystallizing is performed at a temperature range within about 0° C. to about 30° C.; or from about 5° C. to about 15° C.

In some embodiments, methods are provided for purifying oxycodone hydrochloride comprising crystallizing to form purified oxycodone hydrochloride from water or a combination of water and one or more water miscible organic solvents selected from the group consisting of isopropyl alcohol, ethanol, methanol, methyl ethyl ketone and acetone. In some embodiments, the purified oxycodone hydrochloride has less than 0.01% 14-hydroxycodeinone; less than 0.001% 14-hydroxycodeinone; less than 0.0005% 14-hydroxycodeinone; or less than 0.0002% 14-hydroxycodeinone.

In some embodiments, the thebaine starting material is selected or obtained from concentrated poppy straw, anhydrous or raw thebaine alkaloid. In some embodiments, thebaine starting material is obtained from a commercial and/or synthetic source.

In some embodiments, a method is provided for preparation of 14-hydroxycodeinone sulfate or a hydrate thereof comprising exposing thebaine to hydrogen peroxide or peroxyacid and another organic acid in the presence of sodium hydrogen sulfate, sodium sulfate, potassium sulfate, potassium hydrogen sulfate and/or sulfuric acid in an aqueous reaction mixture; and isolating a precipitate of 14-hydroxycodeinone sulfate or a hydrate thereof from the reaction mixture. In some embodiments, the another organic acid is formic acid. In some embodiments, the 14-hydroxycodeinone sulfate has less than 0.05%, 0.025%, or 0.01% of DHC impurity.

In some embodiments, methods are provided for purifying 14-hydroxycodeinone sulfate by a method comprising recrystallization from an aqueous solvent.

In some embodiments, a compound is provided comprising 14-hydroxycodeinone sulfate or a hydrate thereof. The isolated 14-hydroxycodeinone sulfate hydrate is a 14-hydroxycodeinone sulfate hemihydrate, monohydrate, sesquihydrate or dihydrate. 14-hydroxycodeinone hemisulfate monohydrate is provided.

In some embodiments, the isolated 14-hydroxycodeinone sulfate or hydrate thereof exhibits not more than 0.05%, 0.025%, or 0.01% DHC impurity level.

In some embodiments, a method is provided for preparation of oxycodone base from 14-hydroxycodeinone sulfate or a hydrate thereof comprising reducing the 14-hydroxycodeinone sulfate or hydrate thereof in the presence of a catalyst to form oxycodone base. In some embodiments, the oxycodone base is purified to form purified oxycodone base.

In some embodiments, a method is provided for preparation of oxycodone hydrochloride from oxycodone base comprising dissolving oxycodone base in an aqueous organic acid; and adding hydrochloric acid or ammonium chloride to the solution to form oxycodone hydrochloride. In some embodiments, the dissolving comprises complete or partial dissolution of the oxycodone base in the aqueous organic acid. In some embodiments, the aqueous organic acid is selected from tartaric acid, fumaric acid, trifluoroacetic acid, trichloroacetic acid, monochloroacetic acid, lactic acid, glycolic acid, and acetic acid. In some embodiments, the aqueous organic acid is aqueous acetic acid.

In some embodiments, the oxycodone hydrochloride is crystallized by adding water and/or one or more water miscible organic solvents to the oxycodone hydrochloride to form purified oxycodone hydrochloride. In some embodiments, the crystallizing is performed at a temperature range within about 0° C. to about 30° C.; or at a temperature range of from about 5° C. to about 35° C.

In some embodiments, a method is provided for preparation of oxycodone base comprising treating 14-hydroxycodeinone sulfate or a hydrate thereof with calcium acetate or barium acetate to prepare a 14-hydroxycodeinone acetate solution; and reducing the 14-hydroxycodeinone acetate solution to form oxycodone base.

DETAILED DESCRIPTION

Figure 1:
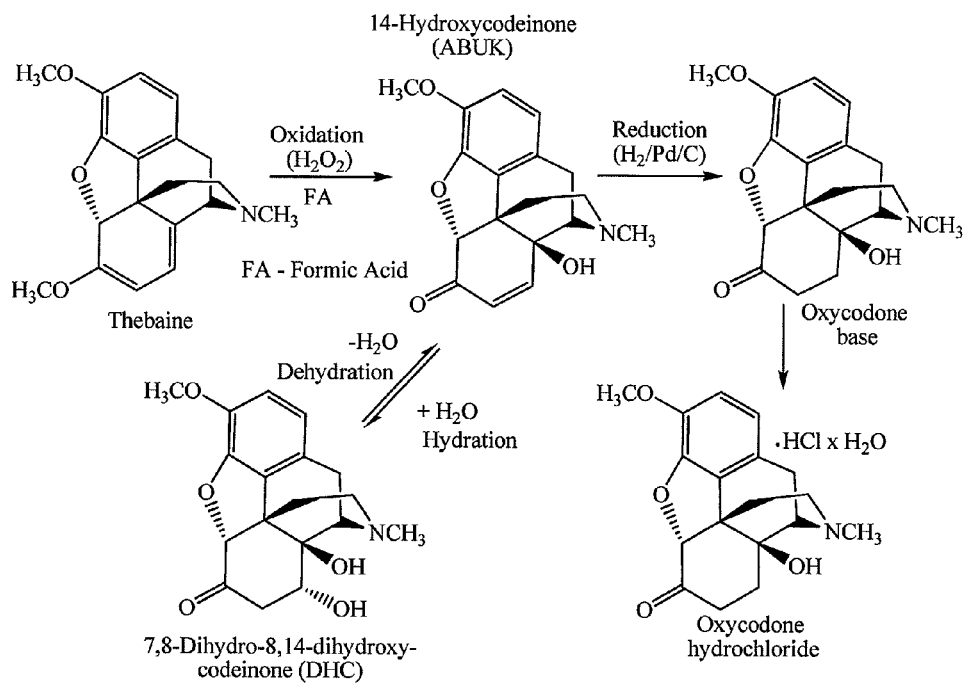
FIG. 1 shows a prior art conventional synthetic route for preparation of oxycodone hydrochloride by oxidation of thebaine to form 14-hydroxycodeinone (ABUK), reduction of 14-hydroxycodeinone to form oxycodone base, and conversion of the base to oxycodone hydrochloride. A synthetic impurity, 7,8-dihydro-8,14-dihydroxycodeinone, (DHC), interconverts by hydration/dehydration from/to 14-hydroxycodeinone. Conventional conversion methods to form oxycodone HCl from oxycodone base using aqueous HCl at elevated temperatures (40-100° C.), or under reflux conditions, can cause acid catalyzed dehydration of residual DHC impurity to form undesirable ABUK in the final product.

Oxycodone hydrochloride is an opioid agonist compound that is valuable as an active pharmaceutical ingredient (API) and as a starting material in the preparation of the opioid antagonists naloxone and naltrexone. Preparation of oxycodone hydrochloride from thebaine through intermediate preparation of 14-hydroxycodeinine is a well-known technology that has been known since 1916. For example, oxidation of thebaine provides intermediate 14-hydroxycodeinone (α,β unsaturated ketone, ABUK), followed by reduction of the ABUK to provide oxycodone base, and finally conversion of oxycodone base provides oxycodone hydrochloride. However, depending on the reagents and reaction conditions employed, various impurities are formed.

As used herein, unless otherwise specified, the term "ABUK", refers to 14-hydroxycodeinone.

During the oxidation of thebaine to give 14-hydroxycodeinone, certain hydrated 14-hydroxycodeinone products can be formed, including 8,14-dihydroxy-7,8-dihydrocodeinone (DHC). The DHC impurity can be carried though the process to the production of oxycodone base. During conversion of oxycodone free base to oxycodone hydrochloride using aqueous hydrochloric acid and heat, the DHC impurity can undergo acid-catalyzed dehydration to be converted into 14-hydroxycodeinone (ABUK). Thus, DHC in oxycodone base can be a source of undesirable ABUK impurity in the final oxycodone hydrochloride. In addition, 6-oxycodol impurities (6α- and/or 6β-oxycodol isomers) can be present in oxycodone base, for example, due to over-reduction of ABUK. In some embodiments, the term oxycodol refers to 6-oxycodol (both 6α- and 6β-oxycodol isomers). In some embodiments, the term 6-oxycodol major isomer refers to 6α-oxycodol.

Synthetic methods that minimize the presence of each of the impurities in final product are desirable. The structures of oxycodone and the impurities oxycodol (2 isomers), DHC, and ABUK are shown in Scheme 1.

Scheme 1

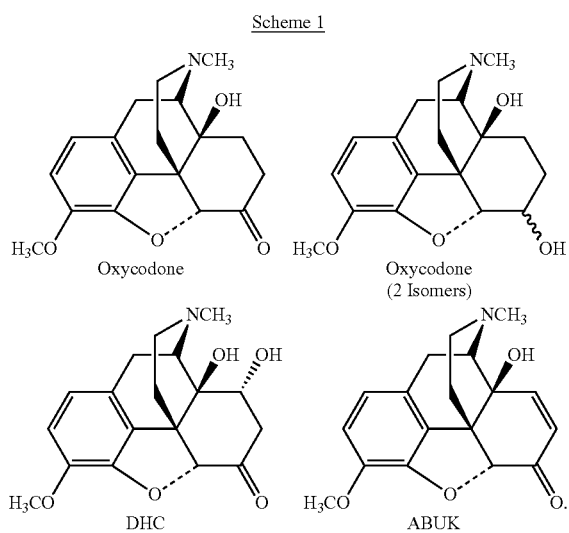

The United States Food and Drug Administration (FDA) has been requesting for over ten years that manufacturers of oxycodone hydrochloride active pharmaceutical ingredient (API) to reduce levels of the impurity 14-hydroxycodeinone in their products. Since at least 2010, the FDA has required that sponsors seeking to market certain oxycodone products use oxycodone hydrochloride API containing not more than 10 parts per million (0.001%) of 14-hydroxycodeinone, or submit data adequately qualifying the impurity for safety.

High ABUK content in oxycodone hydrochloride API can be explained by (1) insufficient reduction of ABUK (product-intermediate of the first synthetic step) to oxycodone base (OC-base) or (2) by conversion of residual amount of the impurity DHC in oxycodone base into ABUK, for example, by acid catalyzed dehydration, during the last step of oxycodone hydrochloride preparation.

Improved methods for commercial synthesis are desirable in order to reduce the impurity profile of oxycodone hydrochloride.

Many of the known 14-hydroxycodeinone (ABUK) preparation procedures provide a preparation of ABUK in the form of ABUK formate salt solution in the aqueous reaction mixture. To separate ABUK from other reactants, side-reaction products, tar and so on, the reaction mixture in these cases is conventionally treated with ammonium or potassium or sodium hydroxides inducing the ABUK base precipitation. Such isolated ABUK base has elevated DHC level (up to 0.5-2.0%) and its further usage as a starting material for the oxycodone preparation is not acceptable because elevated DHC levels in the ABUK base can lead to a high level of ABUK impurity in the final oxycodone hydrochloride product under standard reaction conditions.

In some embodiments, methods are provided herein for conversion of thebaine to 14-hydroxycodeinone sulfate (ABUK sulfate) with minimal formation of the impurity DHC (0-250 ppm), and other impurities, at a conversion rate greater than 99%. In some embodiments, methods are provided for minimizing the amount of DHC in ABUK synthetic intermediate. In some embodiments, pure 14-hydroxycodeinone sulfate intermediate is converted to oxycodone base using a two-stage reduction that minimizes residual ABUK sulfate to undetectable levels; remarkably without significant formation of DHC or other impurities. In some embodiments, the ABUK sulfate is reduced directly to oxycodone without being converted back to its base form. In some embodiments, methods are provided to minimize production and/or presence of oxycodol and other impurities in the oxycodone base. In some embodiments, the disclosure provides methods for preparing oxycodone hydrochloride from oxycodone base without conversion of DHC to ABUK on the final step.

In some embodiments, methods are provided for preparation of oxycodone hydrochloride that minimize or eliminate detectable DHC in oxycodone base.

Figure 8:
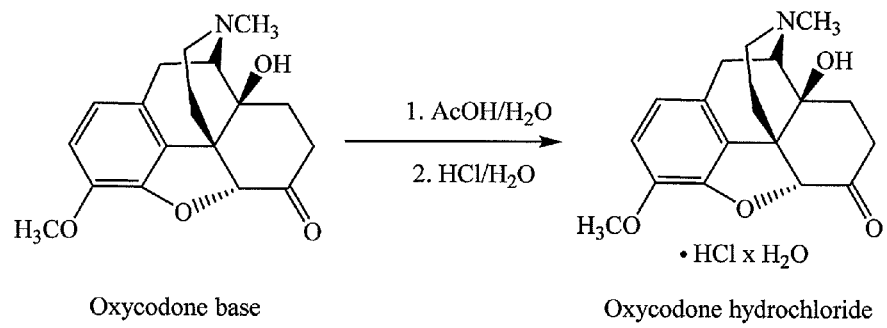
FIG. 8 shows a synthetic route for conversion of oxycodone base to oxycodone hydrochloride.

In some embodiments, methods for converting oxycodone base to oxycodone hydrochloride are provided that minimize or eliminate acid catalyzed dehydration of DHC to ABUK. In some embodiments, methods are provided for converting oxycodone base to oxycodone hydrochloride that minimize acid-catalyzed dehydration of DHC to ABUK comprising dissolving the oxycodone base in an organic acid and water without heating prior to introduction of hydrochloric acid. In some embodiments, methods are provided for converting oxycodone base to oxycodone hydrochloride that minimize acid-catalyzed dehydration of DHC to ABUK comprising dissolving the oxycodone base in an organic acid and water at ambient temperature prior to introduction of hydrochloric acid. In some embodiments, the organic acid is selected from tartaric acid, fumaric acid, lactic acid, trifluoroacetic acid, trichloroacetic acid, monochloroacetic acid, glycolic acid, and acetic acid. In some embodiments, the oxycodone base is dissolved or partially dissolved in organic acid and water, wherein the organic acid is acetic acid, prior to the introduction of HCl for the conversion of oxycodone base to oxycodone HCl, as shown in FIG. 8.

In some embodiments, synthetic methods are provided for the production of highly pure oxycodone hydrochloride API. In some embodiments, the overall process follows four main steps. An outline of the overall process comprising three or four main steps:

1. Oxidation of CPS-ATA to form 14-Hydroxycodeinone Sulfate (ABUK sulfate);
2. Reduction of 14-Hydroxycodeinone Sulfate to crude Oxycodone base;
3. Purification of Crude Oxycodone Base (optional); and
4. Preparation of Oxycodone Hydrochloride and its Crystallization.

Step 1: Oxidation of CPS-ATA to form 14-Hydroxycodeinone Sulfate.

In some embodiments, methods are provided to minimize the amount of DHC impurity in the 14-hydroxycodeinone (ABUK) intermediate. In some embodiments, DHC formation is minimized by preparing the ABUK intermediate as a sulfate salt. In other embodiments, the DHC impurity is further minimized by purification and/or isolation of the 14-hydroxycodeinone sulfate salt. The DHC impurity is undesirable because it can be carried through the process and be converted to ABUK in conventional preparation of oxycodone hydrochloride.

In embodiments, methods are provided for ABUK preparation as an ABUK sulfate salt form. In some embodiments, the ABUK sulfate is isolated. In some embodiments, the ABUK sulfate is isolated as a hydrate. In some embodiments, the ABUK sulfate is isolated in an anhydrous form. In some embodiments, the ABUK sulfate is isolated as a hemihydrate, monohydrate, sesquihydrate or dihydrate. In specific embodiments, the ABUK sulfate is ABUK×0.5H$_2$SO$_4$×2H$_2$O (MW 398.42). In some embodiments, the ABUK sulfate form has not more than 300 ppm, not more than 150 ppm, not more than 100 ppm, not more than 75 ppm, not more than 50 ppm, not more than 25 ppm, or not more than 10 ppm of an 8,14-dihydroxy-7,8-dihydrocodeinone (DHC) impurity. In many instances, DHC was not detectable in ABUK preparations according to the methods provided herein.

In some embodiments, the 14-hydroxycodeinone sulfate is purified by an aqueous treatment and recrystallization. In some embodiments, the ABUK sulfate is re-crystallized from water. In one experiment, recrystallization of impure ABUK sulfate (213 ppm DHC) from water provided ABUK sulfate with 24 ppm DHC in an 81% yield.

Methods are provided for the preparation of oxycodone hydrochloride from a thebaine component selected from synthetic thebaine, concentrated poppy straw, anhydrous or raw thebaine alkaloid (CPS-ATA), or thebaine from various other sources. Thebaine component can be obtained from a commercial source and used directly or further isolated and/or purified prior to use. Thebaine (paramorphine) can be obtained from opium poppies or related species including various strains of *Papaver somniferum, P. orientale* or *P. bracteatum* plants, for example, leaves, roots, pedicels, straw, chaff, head, pod, capsules, seeds or bled latex. Various methods for production of thebaine are known in the art, for example, U.S. Pat. No. 6,723,894 which is incorporated herein by reference. Various routes for the synthesis of thebaine are known, for example, U.S. Pat. Nos. 4,613,668; 4,795,813; 8,067,597, each of which is incorporated herein by reference.

In some embodiments, thebaine starting material is selected from any commercial or synthetic source. In some embodiments, poppy straw or concentrated poppy straw rich in thebaine (CPS-ATA) is employed as an economical source of thebaine component. In some embodiments, the thebaine component is CPS-ATA. In some embodiments, CPA-ATA is used directly as the thebaine component.

In some embodiments, methods are provided for preparation of 14-hydroxycodeinone (ABUK) sulfate from thebaine component. In some embodiments, thebaine component is, for example, CPS-ATA. In some embodiments, methods are provided for preparation of ABUK sulfate comprising mixing thebaine component, water, sodium hydrogen sulfate, formic acid and 30% hydrogen peroxide aqueous solution, and stirring of the prepared mixture at a temperature within the range of from about 50-80° C. until a complete conversion of thebaine into ABUK is detected. In some embodiments, the oxidation reaction is monitored by HPLC. The visible sign of the reaction progress is a massive precipitation of ABUK sulfate from the reaction mixture. At the end of the reaction, an additional amount of water is added for the proper crystallization of the reaction product at ambient temperature. The reaction product is isolated by filtering off precipitated solid material, and product washing with water and acetone mixture, water or ammonium sulfate aqueous solution; followed by drying on filter. The typical yield following washing with acetone/water mixture, for example, 3/1 acetone water, is within the range of from about 70-75% of pure product.

In some embodiments, the method for preparing ABUK sulfate from thebaine component comprises washing wet ABUK sulfate product with ammonium sulfate aqueous solution to prevent ABUK sulfate losses on washings. In some embodiments, cold 40% ammonium sulfate aqueous solution is used in the washing step. In some embodiments, ABUK sulfate product washing on filter with 40% ammonium sulfate aqueous solution ((NH$_4$)$_2$SO$_4$) is employed to increase yield to about 75-80% and prevent product losses due to its high solubility in water or aqueous organic solvents, such as acetone/water mixtures. Although some sulfate salts such as ammonium and sodium sulfate can be present in a minor amount in the ABUK sulfate product, the product is suitable for catalytic reduction for the preparation of oxycodone base.

The filtrate contains impure ABUK, DHC, salts, colored materials and other impurities. In some embodiments, methods for isolation of purified ABUK sulfate from this filtrate are provided. Example 1 provides a representative 30-g scale oxidation process run at 60° C., for less than 6 hours for production of 14-hydroxycodeinone sulfate from thebaine.

Figure 4:
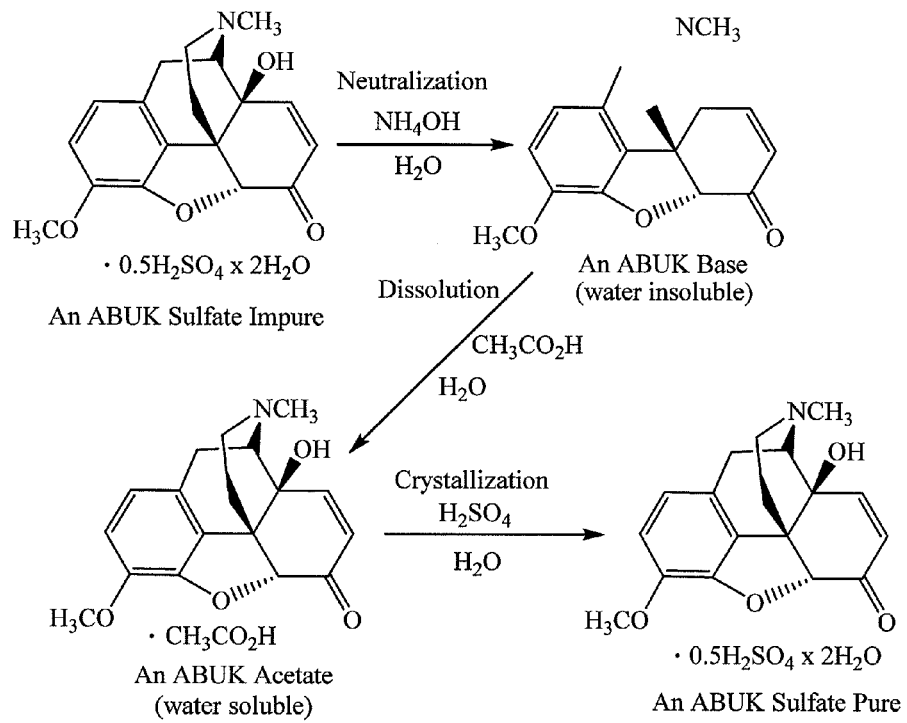
FIG. 4 shows a method for purification of impure 14-hydroxycodeinone sulfate by neutralization to form ABUK base, then dissolution of the base in aqueous acetic acid and crystallization of 14-hydroxycodeinone as a sulfate salt.

In some embodiments, methods are provided for purifying ABUK sulfate. Impure ABUK sulfate intermediate batches can be recycled by this process by neutralization with ammonium hydroxide of mother liquors of either an aqueous solution or impure ABUK sulfate intermediate batches. As shown in FIG. 4, the impure ABUK base can be purified using the crystallization of ABUK in form of sulfate salt that can be used for the oxycodone preparation.

In some embodiments, a method is provided for purifying oxycodone base comprising dissolving impure ABUK base in aqueous acetic acid, treating the solution with sulfate anion sources (sulfuric acid, sodium sulfate, sodium or potassium hydrogen sulfate), and crystallizing ABUK sulfate from the aqueous solution. The crystallized solids are isolated by filtering off, washing and drying. In some embodiments, a method for providing purified ABUK sulfate comprises neutralizing impure ABUK sulfate by addition of water and ammonium hydroxide to provide ABUK base; dissolving the water insoluble ABUK base in aqueous acetic acid to form ABUK acetate; crystallizing ABUK sulfate from water and sulfuric acid, sodium sulfate or potassium hydrogen sulfate; and isolating the purified ABUK sulfate.

Step 2: Reduction of 14-Hydroxycodeinone Sulfate to Crude Oxycodone Base.

In some embodiments, methods are provided for preparing crude oxycodone base with a minimal amount of ABUK and DHC to prevent ABUK formation on the last technological step—oxycodone HCl preparation. In some embodiments, the highest limit of ABUK in the final product is set as 10 ppm.

Figure 3:
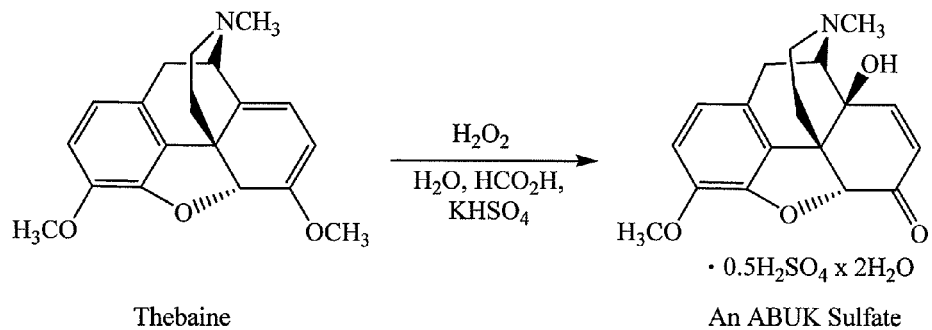
FIG. 3 shows a synthetic route for preparation of 14-hydroxycodeinone sulfate by oxidation of thebaine and treatment with potassium hydrogen sulfate.

Chemically, the reduction step is a catalytical reduction of the ABUK sulfate carbon-carbon double bond with oxycodone formation. In some embodiments, the reduction can employ hydrogen gas or formic acid as reducing agents, as shown in FIG. 3. Catalyst in both cases is a palladium on charcoal (Pd/C) wet catalyst (for example, 10% catalyst, LOD 50%). As a side process, there can be a reduction of ABUK sulfate keto-group and C—C-double to form oxycodol, an impurity in oxycodone hydrochloride. Isomers of oxycodol are shown in Scheme 2.

Scheme 2

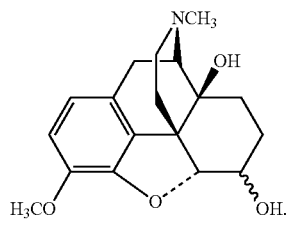

Oxycodol

In case of hydrogen-gas reducing agent, oxycodol can occur in the reaction mixture in amount of about 1.5%. In the case of formic acid as a reducing agent, oxycodol content can be 4 to 6%. In some embodiments, further methods are provided for the isolation and purification of oxycodone base and/or oxycodone hydrochloride in order to remove a significant portion of oxycodol impurity. In some embodiments, the limit of 6α-oxycodol in final oxycodone hydrochloride is set as 0.25% by US Pharmacopeia (USP). Therefore, in some embodiments, methods for minimizing oxycodol content in oxycodone base and oxycodone hydrochloride are provided.

In some embodiments, methods are provided for reducing 14-hydroxycodeinone to oxycodone with minimal impurities, comprising mixing ABUK sulfate in water; reducing the ABUK sulfate with a catalyst and either hydrogen or a hydrogen transfer reagent; filtering off the catalyst with water and/or aqueous acetic acid; neutralizing to basic pH to form oxycodone base; and isolating the oxycodone base. In some embodiments, the pH is adjusted with ammonium hydroxide. In some embodiments, the pH is adjusted with ammonium hydroxide to from about pH 8.0 to about pH 10.5; or from about pH 8.5 to about pH 10.0. In some embodiments, the pH is adjusted with ammonium hydroxide to about pH 9.5.

In some embodiments, the mixing step and/or reducing steps are performed under nitrogen or argon gas.

In some embodiments, the reducing step is performed with a reducing catalyst selected from the group consisting of palladium on active carbon (Pd/C), Pd/C/FeCl$_3$, Pd/C/Fe(III) hydroxide or oxide, Pd/Al$_2$O$_3$, Pt/C, Pt/Al$_2$O$_3$, Pd/BaSO$_4$, Raney Ni-catalysts, Urushibara Ni-catalysts, rhodium on active carbon, Raney nickel, ruthenium black, PtO$_2$, Pt/C and platinum black. In some embodiments, the reducing catalyst is selected from 1-20% palladium on active carbon (Pd/C), Pd/C/FeCl$_3$, Pd/C/Fe(III) hydroxide or oxide; 0.04-10% Pd/Al$_2$O$_3$, 5% Pt/C, 5% Pt/Al$_2$O$_3$, or 5% rhodium on active carbon. In specific embodiments, the reducing step is performed with a palladium on carbon catalyst Pd/C catalyst selected from 2% Pd/C, 2.5% Pd/C, 3% Pd/C, 5% Pd/C, 10% Pd/C, or 5% Pd/BaSO$_4$.

In some embodiments, the reducing step is performed with a regenerable palladium, platinum, rhodium, nickel or ruthenium catalyst. In some embodiments, the catalyst may be either dry or in wet form with e.g. 50% water. In some embodiments, the catalyst is 10% Pd/C (50% L.O.D.). In some embodiments, the reducing catalyst is used in an amount from about 0.01-5 wt %, 0.02-3 wt % or 0.03-1.6 wt % with respect to the starting ABUK sulfate.

In some embodiments, the reducing step is performed with a reducing catalyst as described herein and hydrogen. In some embodiments, the reducing step is performed with a reducing catalyst as described herein and a hydrogen transfer reagent. The hydrogen transfer reagent is used as a hydrogen donor. The hydrogen donor must correspond to the catalyst, therefore formic acid and hypophosphorous acid as well as the salts thereof, such as triethylammonium formate, tri-n-butylammonium formate, sodium formate, potassium formate and ammonium formate as well as sodium hypophosphite are used. In some embodiments, the reducing step employs a catalyst and a hydrogen transfer reagent that is formic acid.

In some embodiments, a method is provided for reducing 14-hydroxycodeinone sulfate to oxycodone base comprising exposing 14-hydroxycodeinone sulfate to a reducing catalyst and hydrogen and/or a hydrogen transfer agent at a temperature of less than 50° C. In some embodiments, the method is performed at less than 45° C. As demonstrated in the examples, the method for reducing 14-hydroxycodeinone sulfate to oxycodone base, even when performed without acetic acid as a co-solvent and without additional reduction treatment of the reaction mixture with formic acid at elevated temperature, surprisingly exhibited higher catalyst selectivity resulting in minimized oxycodol formation in the oxycodone base.

In some embodiments, a method is provided for reducing 14-hydroxycodeinone to oxycodone further comprising one or more catalytic reduction steps. In some embodiments, a method is provided with an additional catalytical reduction step with formic acid as a reducing agent. In some embodiments, the additional catalytical reduction step is performed without intermediate oxycodone base isolation. In some embodiments, the additional catalytical reduction step comprises adding formic acid and additional catalyst to the reaction mixture. In some embodiments, the additional catalytic reduction step is performed at 50-60° C. for about one hour.

In some embodiments, an additional catalytic reduction step is performed with intermediate oxycodone base isolation. In this case, oxycodone crude is isolated from the initial reductive system performed with Pd/C-catalyst. In this case, the additional reduction method further comprises isolating oxycodone base from the reaction mixture by adding ammonium hydroxide solution and filtering to obtain initial crude oxycodone base; converting the initial crude oxycodone base to its formate salt in aqueous solution and treating with formic acid over Pd/C-catalyst at around 50° C. In both cases, good quality crude oxycodone was prepared.

For example, in experiments with hydrogen gas as a reducing agent such as Example 13, a magnetically stirred mixture of ABUK sulfate, water, and Pd/C catalyst was purged with inert gas and hydrogen for 5.25 hours at ambient temperature until 279 ppm ABUK content remained. Formic acid and a fresh portion of Pd/C-catalyst were added to the reaction mixture and reaction was continued at about 50° C. (usually for 1 hour) and then the reaction mixture was cooled down to ambient temperature. In some embodiments, crude oxycodone base is isolated using ammonium hydroxide.

Figure 9:
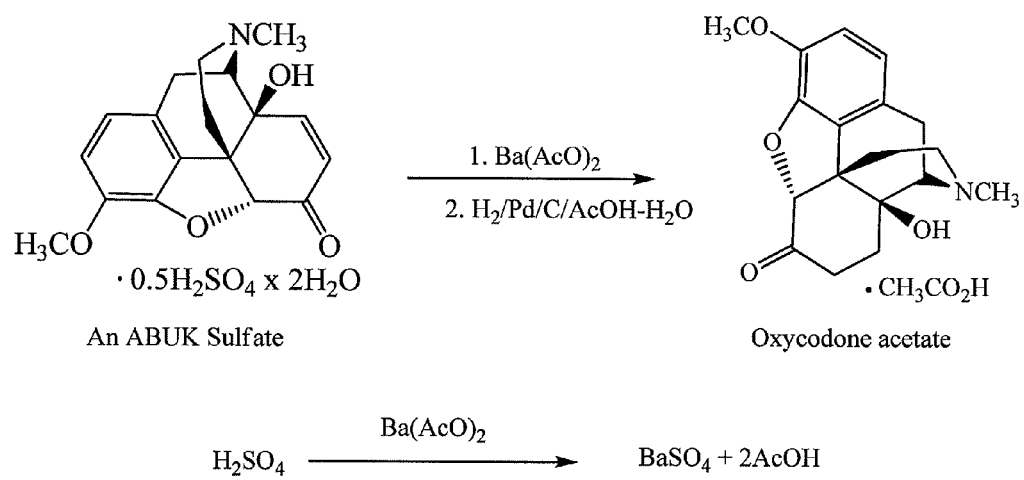
FIG. 9 shows preparation of ABUK solution in acetic acid and hydrogenation to form oxycodone acetate.

In some embodiments, methods are provided for preparing oxycodone acetate by conversion of 14-hydroxycodeinone sulfate to oxycodone acetate, comprising dissolving barium diacetate in aqueous acetic acid to form a solution; adding ABUK sulfate to the solution; filtering the solution; adding a Pd/C catalyst to the filtrate to form a mixture; and hydrogenating the mixture to provide oxycodone acetate, as shown in FIG. 9. In some embodiments, the oxycodone acetate solution is treated with a base to provide oxycodone base. In some embodiments, the oxycodone acetate is treated with ammonium hydroxide to provide oxycodone base.

Selection of Solvent in Reducing Step.

It has been shown that over-reduction of 14-hydroxycodeinone can lead to 6-hydroxy impurities such as 6-oxycodols. For example, Kok and Scammells, employed 5% Pd/BaSO$_4$ or 3% Pd/C as hydrogenation catalysts and performed the reduction of 14-hydroxycodeinone in aqueous acetic acid. In both cases a significant major impurity corresponding to the 6-hydroxy analog was formed due to over-reduction. Changing the solvent to methanol for reduction of either 14-hydroxycodeinone or 14-hydroxycodeinone HCl salt, resulted in a decrease in the formation of the 6-hydroxy by-product using either catalyst. See Table 1 in Kok and Scammell, RSC Adv. 2012, 2, 11318-11325, which is incorporated herein by reference. In some embodiments, the reduction is performed in a solvent selected from one or more of water, acetic acid, aqueous acetic acid, aqueous formic acid, ethanol, or methanol.

Step 3: Purification of Crude Oxycodone Base.

In some embodiments, oxycodone base crude is converted directly into oxycodone hydrochloride. In some embodiments, oxycodone base is purified prior to converting to oxycodone hydrochloride. In some embodiments, methods are provided for purifying crude oxycodone base to remove process impurities. In some embodiments, oxycodone base is purified by a process comprising crystallizing, recrystallizing or triturating the crude oxycodone base in a solvent. In some embodiments, methods for producing oxycodone hydrochloride comprise purifying oxycodone base by treating with an organic solvent. In some embodiments, the organic solvent is a water-miscible solvent selected from ethanol, acetone or isopropyl alcohol. In some embodiments, the organic solvent is a combination of a halogenated solvent and a water miscible solvent. In some embodiments, oxycodone base is dissolved in a halogenated solvent prior to adding one or more water miscible solvents. In some embodiments, the organic solvent is a combination of a water miscible solvent with a halogenated solvent, wherein the halogenated solvent is selected from chloroform, or dichloromethane. In some embodiments, the water miscible solvent is selected from any water miscible solvent known in the art. In some embodiments, the water miscible solvent is selected from one or more of methanol, ethanol, isopropyl alcohol, methyl ethyl ketone, acetone, ethylene glycol, propylene glycol, monomethyl- or monoethyl ethers of ethylene- or propylene glycols. In some embodiments, the organic solvent is selected from methanol or isopropyl alcohol. In some embodiments, the organic solvent is a mixture of methanol and isopropyl alcohol. In some embodiments, the organic solvent is isopropyl alcohol. In some aspects, methods for oxycodone base purification are provided comprising treating the crude oxycodone base with isopropyl alcohol to provide oxycodone base with reduced levels of impurities.

In some embodiments, methods are provided for purifying crude oxycodone base to remove process impurities comprising crystallizing, recrystallizing or triturating the crude oxycodone base in a solvent that is a mixture of one or more water miscible organic solvents.

In some embodiments, methods are provided for purifying crude oxycodone base to remove process impurities comprising crystallizing, recrystallizing or triturating the crude oxycodone base in a solvent that is a mixture of water and one or more water miscible organic solvents in a ratio within from about 5 to 95 vol %, 10 to 70 vol %, 20 to 60 vol %, or 30 to 50 vol % with water. In some embodiments, the solvent for the oxycodone base purification is a mixture of one or more water miscible organic solvents at about 20 vol %, 30 vol %, 35 vol %, 45 vol % or 50 vol % water miscible organic solvents in water.

In some embodiments, a method for purifying oxycodone base comprises treating oxycodone base with one or more organic solvents, or one or more organic solvents and water.

In some embodiments, oxycodone base is purified in a water/organic solvent system to economize on use of organic solvent.

In some aspects, oxycodone base is treated with a mixture of water and isopropyl alcohol; a mixture of water, isopropyl alcohol and propylene glycol; a mixture of water, isopropyl alcohol and methoxyethanol; or a mixture of water, isopropyl alcohol and ethylene glycol. In some aspects, the method comprises treating oxycodone base with a mixture of water and isopropyl alcohol in a ratio of about 2:1 (v/v). In some aspects, the method comprises treating oxycodone base with a mixture of water/isopropyl alcohol/propylene glycol in a ratio of about 6:2:3 (v/v). In some aspects, the method comprises treating oxycodone base with a mixture of water/isopropyl alcohol/methoxyethanol in a ratio of about 6:1:3 (v/v).

In one aspect, a method is provided for purifying crude oxycodone base, the method comprising transferring isolated crude oxycodone base into a reaction vessel with isopropyl alcohol; and refluxing the oxycodone base with isopropyl alcohol to provides crystalline purified oxycodone base. The product is obtained by filtering, rinsing with IPA and drying to provide purified oxycodone base that is suitable for the oxycodone hydrochloride preparation step.

In another aspect, a method is provided for purifying crude oxycodone base, the method comprising completely dissolving crude oxycodone base in small volume of chloroform or chlorofoim/methanol mixture; diluting the mixture with isopropyl alcohol to form a homogenous mixture; distilling off the chloroform under nitrogen and precipitating the crystalline oxycodone base from isopropyl alcohol. The crystalline oxycodone base is filtered, rinsed with isopropyl alcohol and dried to provide purified oxycodone base, suitable for the oxycodone hydrochloride preparation step.

In some embodiments, methods are provided for preparing oxycodone base with not more than 0.25%, 0.20%, 0.15%, 0.10%, 0.05%, or 0.025% DHC. For example, oxycodone base crude comprising 0.0202% DHC was obtained by reducing 14-hydroxycodeinone sulfate in water without any purification.

In some embodiments, methods are provided for preparing oxycodone base with not more than 0.50%, 0.25%, 0.15%, 0.10%, total 6-oxycodol.

In some embodiments, methods are provided for preparing oxycodone base with not more than 0.1%, 0.010%, 0.005%, 0.002%, or 0.001% (less than 10 ppm) ABUK.

Step 4: Preparation and Crystallization of Oxycodone Hydrochloride.

Conventional conversion of oxycodone base to oxycodone HCl using aqueous HCl is typically performed at elevated temperatures, such as at a temperature greater than about 50° C., greater than about 55° C., greater than about 60° C., or at about 70° C. up to 100° C., or higher.

However, directly converting oxycodone base to oxycodone hydrochloride with strong acid and elevated temperature conditions may provoke acid catalyzed dehydration of DHC impurity to ABUK.

In some embodiments, in order to avoid DHC conversion into ABUK at the final oxycodone hydrochloride preparation step, methods are provided that avoid use of both strong acid (HCl) and high temperature.

In some embodiments, methods are provided for minimizing ABUK formation due to residual DHC in oxycodone base in the last technological step of oxycodone HCl preparation.

In some embodiments, methods are provided for converting oxycodone base to oxycodone hydrochloride comprising converting oxycodone base to oxycodone acetate, and exposing the oxycodone acetate to HCl.

In some embodiments, a method is provided for preparation of oxycodone hydrochloride from oxycodone base comprising dissolving oxycodone base in an aqueous organic acid; and adding hydrochloric acid or ammonium chloride to the solution to form oxycodone hydrochloride. In some embodiments, the dissolving comprises complete or partial dissolution of the oxycodone base in the aqueous organic acid. In some embodiments, the aqueous organic acid is selected from tartaric acid, fumaric acid, lactic acid, trifluoroacetic acid, trichloroacetic acid, monochloroacetic acid, glycolic acid, and acetic acid. In some embodiments, the aqueous organic acid is aqueous acetic acid.

In some embodiments, methods are provided for converting oxycodone base to oxycodone hydrochloride comprising dissolving oxycodone base in aqueous organic acid at a temperature below 50° C., below 40° C., or below 30° C., to form an oxycodone organic acid salt in situ, and exposing the oxycodone organic acid salt to HCl or ammonium chloride.

In some embodiments, the oxycodone organic acid salt is oxycodone acetate.

In some embodiments, methods are provided for converting oxycodone base to oxycodone hydrochloride comprising dissolving oxycodone base in aqueous acetic acid at a temperature below 50° C., below 40° C., or below 30° C., to form oxycodone acetate in situ, and exposing the oxycodone acetate to HCl as shown in FIG. 8.

In some embodiments, the oxycodone acetate is isolated or utilized in situ to form an oxycodone organic acid salt or an oxycodone inorganic acid salt.

In some embodiments, the oxycodone inorganic acid salt is selected from oxycodone hydrochloride, hydrobromide, hydrofluoride, phosphate, sulfate, or nitrate. In some embodiments, the oxycodone inorganic acid salt is selected from oxycodone hydrochloride, oxycodone hydrobromide, or oxycodone sulfate. In some embodiments, the oxycodone inorganic acid salt is oxycodone hydrochloride.

In some embodiments, the oxycodone organic acid salt is selected from organic acid salts such as terephthalate, citrate, lactate, glycolate, tartrate, maleate, fumarate, mandelate, acetate, dichloroacetate, trifluoroacetate, oxalate, formate, succinate, and the like; and amino acid salts such as aspartate, glutamate and the like.

In some embodiments, the oxycodone organic acid salt is oxycodone acetate or oxycodone terephthalate. In some embodiments, the oxycodone organic acid salt is oxycodone acetate.

In some embodiments, methods are provided for preparing oxycodone hydrochloride with not more than 200 ppm (0.02%); 150 ppm (0.015%); 100 ppm (0.01%); 75 ppm (0.0075%); 50 ppm (0.005%) or 25 ppm (0.0025%) 14-hydroxycodeinone. In some embodiments, oxycodone hydrochloride is provided with not more than 10 ppm, 5 ppm, 3 ppm, 2 ppm or 1 ppm 14-hydroxycodeinone.

FDA guidelines provide a limit of not more than 0.001% of API (10 parts per million (ppm)) as the acceptable level of 14-hydroxycodeinone impurity in oxycodone HCl. In some embodiments, methods are provided for preparing oxycodone HCl with not more than 0.01%, 0.0075%, 0.005%, 0.001%, 0.0005%, 0.0003%, 0.0002%, or 0.0001% 14-hydroxycodeinone.

In some embodiments, methods are provided for preparing oxycodone hydrochloride with not more than 10 ppm, 5 ppm, 3 ppm, 2 ppm, or 1 ppm 14-hydroxycodeinone. In other embodiments, oxycodone hydrochloride is provided with not more than 10 ppm, 5 ppm, 3 ppm, 2 ppm, or 1 ppm 14-hydroxycodeinone impurity.

In some embodiments, methods are provided for preparation of crystalline oxycodone hydrochloride (the final product) in order to minimize residual impurities including ABUK, oxycodol, and DHC.

The USP acceptance criteria for oxycodone hydrochloride is not more than 0.25% 6-α Oxycodol. In some embodiments, methods are provided for preparation of oxycodone hydrochloride with not more than 0.25%, 0.20%, 0.15%, 0.10%, 0.05%, 0.02%, or 0.01% 6-α Oxycodol impurity.

The USP acceptance criteria for oxycodone hydrochloride is not more than 0.15% 7,8-dihydro-8β-14-dihydroxycodeinone. In some embodiments, methods are provided for preparing purified oxycodone hydrochloride with not more than 0.15%, 0.10%, 0.05%, or 0.01% of an 8,14-dihydroxy-7,8-dihydrocodeinone (DHC) impurity.

In some embodiments, methods are provided for conversion of oxycodone base to oxycodone hydrochloride comprising dissolving the oxycodone base in aqueous acetic acid; followed by treating the oxycodone acetate in solution with ammonium chloride. In some embodiments, one equivalent of ammonium chloride is employed. This method avoids both use of strong acid HCl and use of elevated temperature and thus provides oxycodone hydrochloride with a minimal amount of ABUK impurity.

In some embodiments, methods are provided for conversion of oxycodone base to oxycodone hydrochloride comprising dissolving or partially dissolving the oxycodone base in aqueous organic acid, so as to avoid elevated temperature. In some embodiments, methods are provided for conversion of oxycodone base to oxycodone hydrochloride comprising dissolving the oxycodone base in aqueous organic acid at a temperature less than 50° C., less than 45° C., less than 40° C., or preferably less than 30° C., or at ambient temperature. In some embodiments, methods are provided for conversion of oxycodone base to oxycodone hydrochloride comprising dissolving the oxycodone base in aqueous acetic acid at not more than 50° C., 45° C., 40° C., 30° C., or at ambient temperature.

In some embodiments, methods are provided for conversion of oxycodone base to oxycodone hydrochloride comprising dissolving or partially dissolving the oxycodone base in aqueous organic acid, wherein the aqueous organic acid is present in greater than about 1.1, 1.2, 1.3, 1.4, 1.5, 2, 3-fold, or more, molar equivalents excess compared to mols of oxycodone base.

In some embodiments, methods are provided for conversion of oxycodone base to oxycodone hydrochloride comprising dissolving or partially dissolving the oxycodone base in aqueous organic acid, wherein the aqueous organic acid is present in about 1, or about 0.9, 0.8, 0.7, 0.5-fold, or less, molar equivalents compared to mols of oxycodone base.

Surprisingly, it has been found that performing the conversion of oxycodone base to oxycodone hydrochloride by a method comprising dissolving oxycodone base in aqueous organic acid at ambient temperature; followed by treating with hydrochloric acid at ambient temperature provides oxycodone hydrochloride with not more than 0.01%, 0.0075%, 0.005%, 0.001%, 0.0005%, 0.0003%, or 0.0002% 14-hydroxycodeinone.

Figure 6:
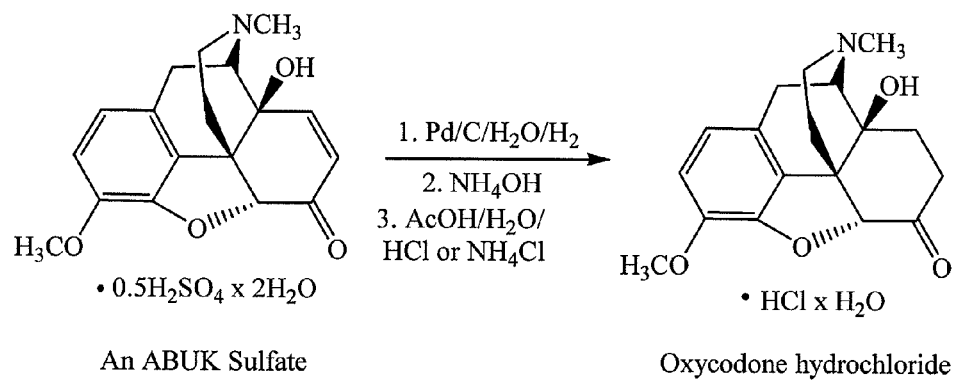
FIG. 6 shows methods for preparing oxycodone hydrochloride from 14-hydroxycodeinone sulfate.

In some embodiments, a method is provided for preparing oxycodone hydrochloride from 14-hydroxycodeinone sulfate, comprising reducing the 14-hydroxycodeinone sulfate in the presence of a catalyst to form oxycodone base; dissolving, or partially dissolving, the oxycodone base in an aqueous organic acid to form an oxycodone organic acid salt, and adding hydrochloric acid or ammonium chloride to the oxycodone organic acid salt to form oxycodone hydrochloride, for example, as shown in FIG. 6.

Figure 7:
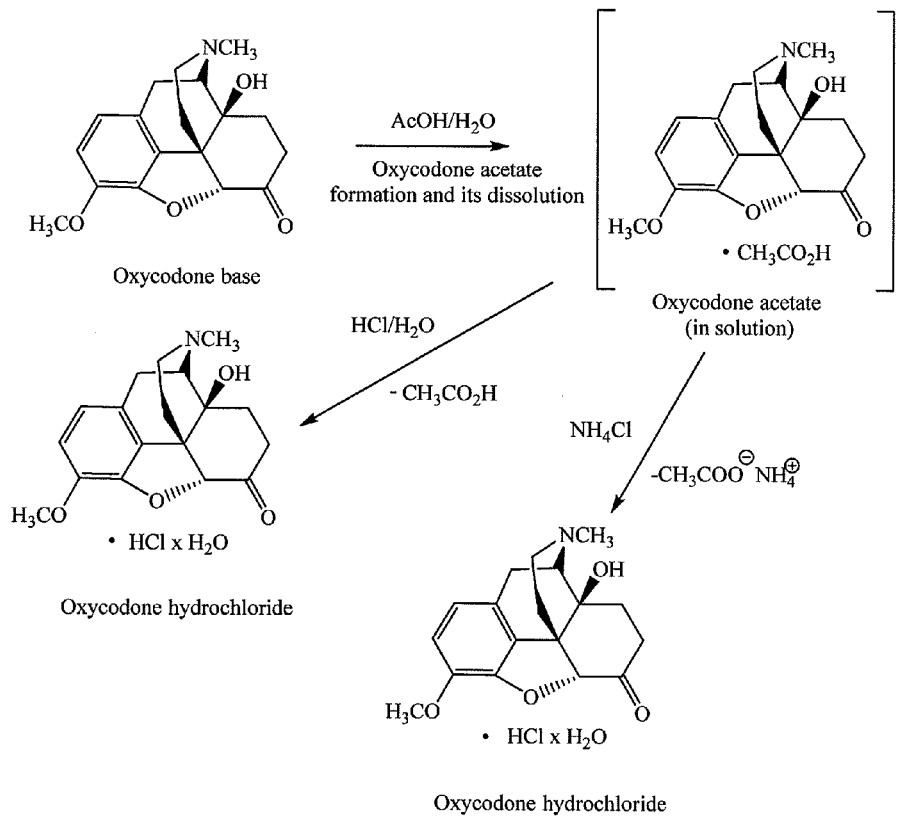
FIG. 7 shows two methods for conversion of oxycodone base to oxycodone hydrochloride via oxycodone acetate and either HCl or ammonium chloride.

In some embodiments, a method is provided for preparation of oxycodone hydrochloride comprising forming oxycodone acetate from oxycodone base in situ, followed by treatment with an aqueous solution of hydrochloric acid or ammonium chloride, for example, as shown in FIG. 7.

In some embodiments, methods are provided for conversion of oxycodone base to oxycodone hydrochloride in aqueous-acetic acid media that result in fewer amounts of one or more impurities in the final product, compared to conventional conversion methods. In some embodiments, preparation of oxycodone hydrochloride from purified oxycodone base comprises mixing purified oxycodone base, water and acetic acid until a clear or almost clear homogenous aqueous oxycodone acetate solution is obtained. In some embodiments, the oxycodone acetate in solution is treated with a small excess (15-20%) of concentrated hydrochloric acid at ambient temperature. The oxycodone hydrochloride crystallizes for about one hour, and then the crystallizing mixture is diluted with IPA or other organic water miscible solvent (MEK for example) using magnetic stirring. The product is filtered off, washed on filter with IPA and acetone, and then dried on filter. The oxycodone hydrochloride product contains less than 10 ppm of 14-hydroxycodeinone.

In some embodiments, a method is provided for preparation of oxycodone hydrochloride from purified oxycodone base comprising generating oxycodone acetate in solution and treating with about one equivalent of ammonium chloride at ambient temperature to provide oxycodone hydrochloride.

In some embodiments, a method for preventing or minimizing acid catalyzed dehydration of DHC to ABUK in the conversion of oxycodone base to oxycodone hydrochloride is provided. In some embodiments, the oxycodone base is dissolved without heating in acetic acid and water; then HCl or ammonium chloride is added to effect conversion to oxycodone hydrochloride. In some embodiments, an organic solvent is added to crystallize oxycodone hydrochloride. In some embodiments, the organic solvent is selected from isopropyl alcohol, ethanol, methanol, acetone, or methyl ethyl ketone. In some embodiments, the conversion step is performed at a temperature between from about 0° C. to about 50° C.; at a temperature between from about 10° C. to about 40° C.; or at a temperature between from about 15° C. to about 35° C. In some embodiments, the conversion step is performed at ambient temperature.

In some embodiments, crystallization of oxycodone hydrochloride is provided by addition of water or water and a combination of one or more organic water miscible solvents. In some embodiments, the one or more organic water miscible solvents are selected from one or more of isopropyl alcohol, methyl ethyl ketone, and acetone. In some embodiments, crystallization of oxycodone hydrochloride is performed at a temperature between from about 0° C. to about 50° C., between about 10° C. to about 40° C.; from about 15° C. to about 35° C.; or at about ambient temperature.

EXAMPLES

Methods are provided for the production of oxycodone hydrochloride with the goal of minimizing one or more process impurities. The presence and quantification of process impurities in starting materials, intermediates and final product was detected by HPLC and associated methods. Generally, reverse phase HPLC was employed for detection and quantification of impurities. Various HPLC methods were employed as described.

In general, samples for injection were dissolved in 0.85% phosphoric acid aqueous solution. Buffer was prepared from sodium dihydrogen phosphate monohydrate (3.45 g in 1000 mL of water). Dodecyl sulfate sodium salt (5.4 g) was added and pH was adjusted with triethylamine to pH 7.9. Mobile phase consisted of buffer (730 mL), acetonitrile (150 mL) and methanol (120 mL). The pH of the mobile phase was adjusted to pH 8.5 or 9.5 with 25% NaOH. Injection volume was 7 to 50 microliters. HPLC was run at 1.0 mL per minute under isocratic conditions with UV monitoring at 220 nm at a column temperature of 45 C. Column Gemini-NX C-18, 150 mm×4.6 mm, 5 urn. Runtime was 30 minutes. Use of these conditions provided elution order of DHC, ABUK, α-oxycodol, β-oxycodol and oxycodone standards at retention times over 8-25 min.

An HPLC normalization method was an HPLC analysis method based on the assumption that area of all HPLC peaks equal 100%, where the highest oxycodone peak value is in the linear range of 1.00-1.50 units (absorbance units). DHC was evaluated using pH 8.5 mobile phase, ABUK was evaluated with pH 9.5 mobile phase. The typical sample concentration was around 0.3-2.0 mg/mL, and an injection volume was 7 to 50 μL. Generally, the normalization method was employed for the routine preparative work. Unless otherwise specified, HPLC values provided herein are obtained by the area Normalization method.

An R&D HPLC Assay method for quantification of ABUK was employed based on determination of HPLC response of exact concentration (amount) from a standard injection (typical standard concentration was 8.24 μg/mL, injection volume –10 μL), and determination of HPLC response of oxycodone sample injection (typical concentration 30-40 mg/mL, injection volume is 50 μL) and further proper calculations based on AUC comparison.

An R&D HPLC Assay method for determination of DHC and oxycodol was based on the assumption that responses (extinction coefficient) of DHC and oxycodol are the same as of ABUK or oxycodone and a direct comparison of areas of corresponding peaks (ABUK, DHC or oxycodol) was employed.

A QC Method HPLC Assay was employed for quantification of ABUK in a sample based on comparison of area ABUK peak of the sample and the same of sample plus known amount of ABUK standard mixture.

The ABUK R&D Assay method was more sensitive than normalization method by factor around 450 (considering concentration and volume of injected analyte), but the normalization method was employed as more convenient for the routine preparative work.

Example 1

14-Hydroxycodeinone Sulfate Preparation from Thebaine

Figure 2:
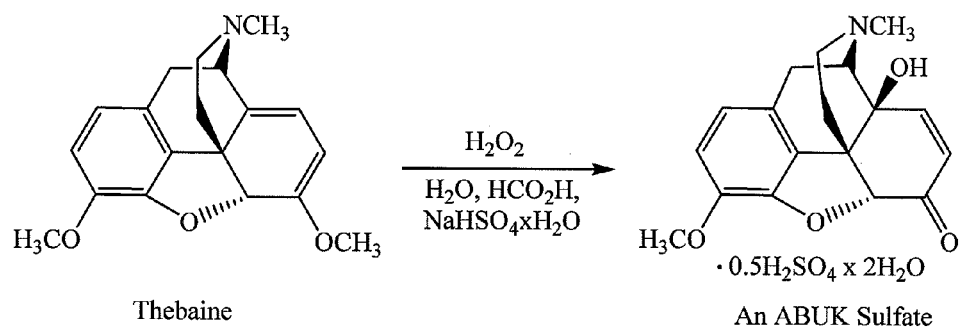
FIG. 2 shows a synthetic route for preparation of 14-hydroxycodeinone sulfate by oxidation of thebaine and treatment with sodium hydrogen sulfate.

14-Hydroxycodeinone sulfate was prepared by oxidation of thebaine as shown in FIG. 2. A 250 mL jacketed reactor was charged with CPS-thebaine (Assay 75.7%; 39.63 g; 96.35 mmol; equivalent to 30.0 g of 100%), NaHSO$_4$ monohydrate (13.57 g, 98.28 mmol), and a solution of DI water (10.25 g) and 97% formic acid (5.26 g, 110.80 mmol).

The mixture was stirred at 20° C. for 15 minutes to provide a brownish to gray easily stirrable mixture. Hydrogen peroxide (30%, 11.8 mL, 115.62 mmol) was added to the stirred reaction mixture at 20° C. over 7 minutes. After the addition was completed, temperature of the reaction mixture was kept at 20° C. with magnetic stirring for about 15 minutes and then the reaction mixture was heated to 60° C., over a time period of about 30 minutes. Stirring was continued for 5.75 hours until complete conversion from thebaine into 14-hydroxycodeinone was observed by HPLC, as shown in Table 1. HPLC Normalization Data, was provided using a 15 cm×4.6 mm Phenomenex NX-C18, 5 μm column.

TABLE 1

Thebaine Oxidation Reaction Progress and Impurity Profile.

| Time Event | Thebaine (%) | 14-OH-Codeinone (ABUK) (%) | DHC (%) |
|---|---|---|---|
| 3.50 hours oxidation | 11.83 | 88.10 | ND |
| 4.20 hours oxidation | 5.71 | 94.23 | ND |
| 5.20 hours oxidation | 0.14 | 99.37 | 0.0342 |
| ABUK Sulfate isolated dry | NA | 99.89 | ND |

ND = not detected.

A precipitation of yellow solids occurred after 2.5 hours of stirring at 60° C. The reaction mixture was cooled to 35° C. over a period of 20 minutes, and water (50 mL) was added to the crystallizing mixture. Then temperature was lowered to 30° C. over a period of 20 minutes. Stirring continued for 50 minutes at 30° C. till additional crystallization occurred. The mixture was cooled further till 20° gradually over one hour, kept at 20° for 0.5 hour and solids were filtered off, washed on filter with water (2×15 mL). The resultant 14-hydroxycodeinone (ABUK) sulfate yellow solids were dried on filter till constant weight (24.95 g, 62.62 mmol, 65% yield, 99.89% purity by HPLC Normalization Method.). No starting thebaine and no DHC impurity were detected by HPLC normalization method as shown in Table 1.

Example 2

Characterization of 14-Hydroxycodeinone Sulfate

To determine molecular formula, 14-Hydroxycodeinone (ABUK) sulfate (Lot B) and 14-hydroxycodeinone (ABUK) base (Lot A) were analyzed by HPLC. As shown in Scheme 3, ABUK sulfate molecular formula was determined to be ABUK×0.5H$_2$SO$_4$×2H$_2$O (molecular weight 398.42), as shown in Table 2.

ABUK sulfate and ABUK base samples were analyzed with HPLC. A solution of each sample of ABUK base and ABUK sulfate was analyzed three times (three injections), HPLC responses were corrected according to Karl Fischer water content analysis (10.7% of water in ABUK sulfate sample: 9.04% is water in ABUK sulfate crystals and 1.66% is "absorption" water). HPLC data correlate with ABUK×0.5H$_2$SO$_4$×2H$_2$O (molecular weight 398.42) as a molecular formula.

5.15 (bs, 1H), 4.72 (s, 1H), 3.86 (s, 3H), 3.20 (d, J=18 Hz, 1H), 3.05 (d, J=6 Hz, 1H), 2.37-2.61 (m, 6H), 2.23-2.37 (m, 1H), 1.66-1.75 (m, 1H).

Figure 11:
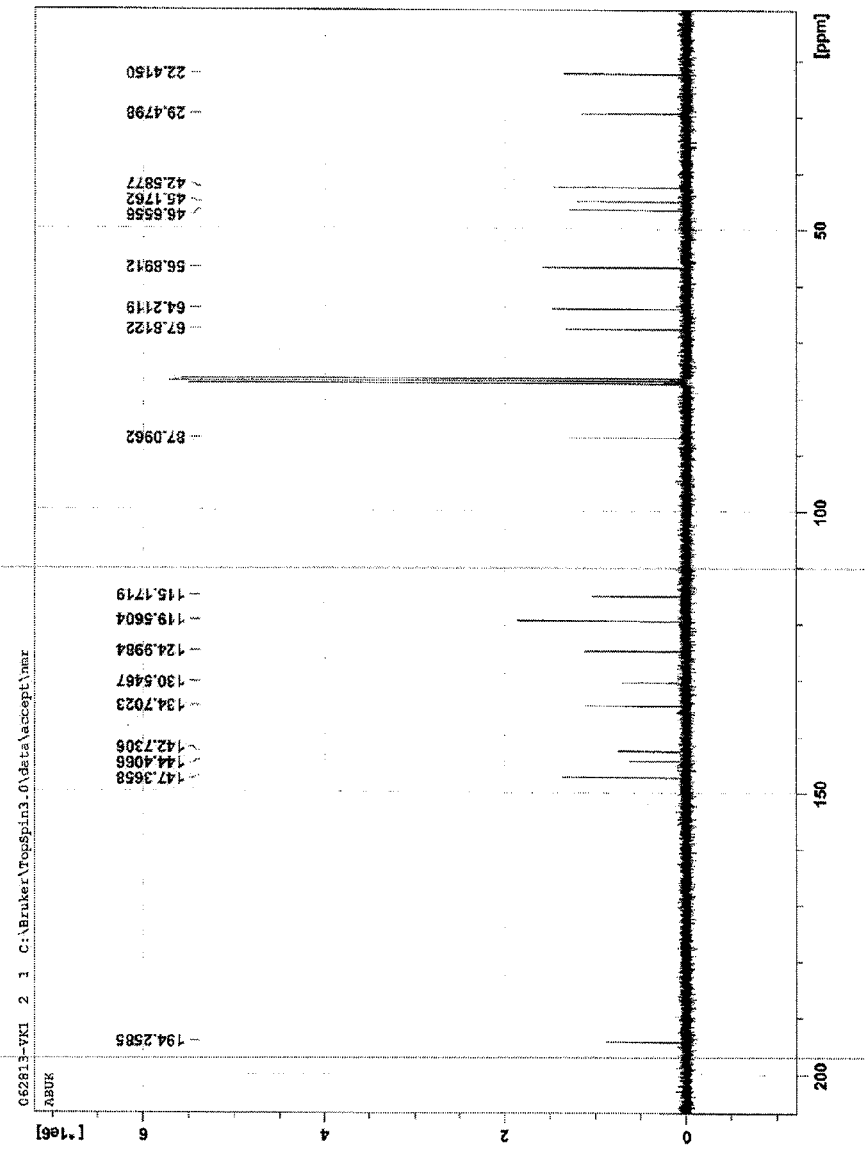
FIG. 11 shows a $^{13}$C NMR Spectrum of 14-hydroxycodeinone base.

Analysis by $^{13}$C-NMR confirmed identity of the ABUK base (Lot A), as shown in FIG. 11. $^{13}$C-NMR 75 MHz, (CDCl$_3$) δ: 194.26, 147.37, 144.41, 142.73, 134.70, 130.55, 125.00, 119.56, 115.17, 87.10, 67.81, 64.21, 56.89, 46.66, 45.18, 42.59, 29.48, 22.42 ppm.

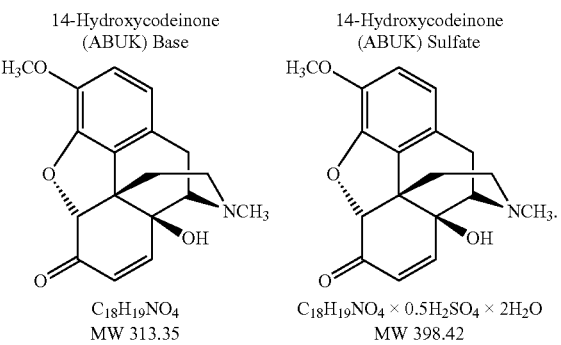

Scheme 3

Example 3

Preparation of 14-Hydroxycodeinone Sulfate from Thebaine with Potassium Hydrogen Sulfate A 250 mL jacketed reactor was subsequently charged with thebaine (311.37 g/mol, 30.0 g, 96.35 mmol), solution of

TABLE 2

| | HPLC Analysis for Determination of Molecular Formula. | | | | | |
|---|---|---|---|---|---|---|
| Lot Number | ABUK Form | conc., mg/g | injection volume, μL | HPLC Response | HPLC Purity, % | Response per μL and conc. | Avg. |
| Lot A | ABUK Base MW 313.35 | 0.673 | 9 | 98.19 | 100.00 | 16.21 | 16.29 |
| | | | 9 | 98.70 | 100.00 | 16.30 | |
| | | | 9 | 99.05 | 100.00 | 16.35 | |
| Lot B | ABUK Sulfate MW 398.42 | 0.832 | 9 | 92.90 | 98.51 | 12.59 | 12.58 |
| | | | 9 | 92.74 | 98.92 | 12.52 | |
| | | | 9 | 93.06 | 98.45 | 12.62 | |

Karl Fischer analysis indicated that the ABUK Sulfate sample Lot B had 1.66% "absorption" water. So, a response per μL (volume) and concentration value (12.58) was multiplied by 1.0166 to obtain 12.79 value for the appropriate correction. Ratio of MW's (molecular weights)=398.42/313.35=1.27; ratio of responses 16.29/12.79=1.27. ABUK Sulfate molecular formula was thus determined to be ABUK×0.5H$_2$SO$_4$×2H$_2$O (molecular weight 398.42).

HPLC Analysis of the ABUK base (Lot A) confirmed the identity and purity (100%) of the sample as shown in Table 2. HPLC t$_r$=5.926 min. (Normalization method, R&D).

HPLC Analysis of the ABUK sulfate (Lot B) confirmed the identity and purity (98.51%) of the sample as shown in Table 2. HPLC 4=5.929 min (Normalization Method R&D).

Figure 10:
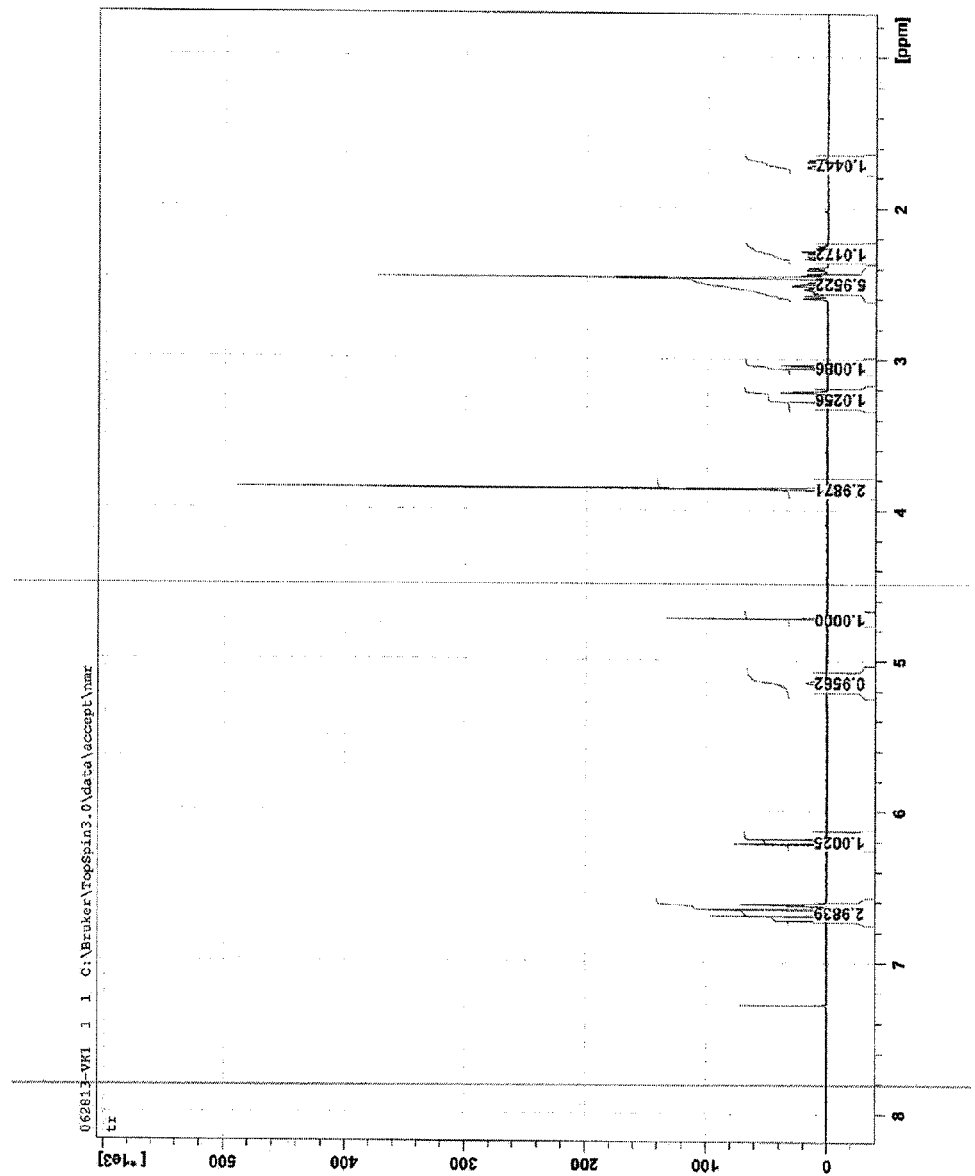
FIG. 10 shows $^1$H NMR Spectrum of 14-hydroxycodeinone base.

Analysis by proton NMR confirmed the identity of the ABUK base (Lot A), as shown in FIG. 10. $^1$H-NMR 300 MHz, (CDCl$_3$), δ: 6.60-6.70 (m, 3H), 6.20 (d, J=10 Hz, 1H), KHSO$_4$ (14.1 g, 100.44 mmol) in DI water (40 ml) and 97% formic acid (5.2 mL, 133.61 mmol). The mixture was warmed to 30° C. (Julabo thermostat) and stirred for 20 min to give yellow to light brown almost homogeneous pale solution. Hydrogen peroxide (30%, 13.5 mL, 119.12 mmol) was added to the stirred reaction mixture at 30-31° C. over 25 minutes. After the addition was completed, temperature of the reaction mixture was kept at 30° C. for 25 minutes, increased to 50° C. with stirring over 10 minutes and kept 9 hours at 50-51° C. until the thebaine was completely converted into 14-hydroxycodeinone. The precipitation of the yellow solids occurred after 7 hours stirring at 50° C. Water (10 mL) was added to the reaction mixture and the reaction mixture was cooled down to 20° C. and stirred at this temperature for 14 hours (overnight). The solid material was filtered off, washed on filter with icy water (2×20 mL), IPA (2×30 mL) and MTBE (2×40 mL) and dried on filter to provide 14-hydroxycodeinone sulfate (27.81 g, 69.80 mmol, 72.4% yield).

Example 4

Recrystallization of Crude 14-hydroxycodeinone Sulfate

A 125 mL jacketed reactor, equipped with a mechanical stirrer, was subsequently charged with 14-hydroxycodeinone sulfate (Lot C, 14.53 g) and water (60 mL). The mixture was heated up to 60° C., hold at this temperature, cooled down to 30° C., diluted with additional 10 mL of water, cooled down to 0° C., hold at 0° C. for 40 minutes. The time—temperature profile of the crystallization is shown in the Table 3.

TABLE 3

Time-Temperature Profile of the Recrystallization of ABUK sulfate.

| Event | Current Time, minutes, temperature, operation time (min) | Added Water, mL | Notes, Stirrer RPM |
|---|---|---|---|
| 14-hydroxycodeinone sulfate, Lot C - Water Mixing and Heating to 60° C. | 0.0 (20° C.)-25 (60° C.), 25 min | 60 | The crystallizing mixture is fluid, 100 RPM |
| 60° C. Holding | 25 (60° C.)-35 (60° C.) 10 min | 0.0 | The crystallizing mixture is less fluid, 200 RPM |
| Cooling Down to 30° C. | 35 (60° C.)-65 (30° C.) 30 min. | 0.0 | The crystallizing mixture is less fluid, 200 RPM |
| 30° C. Reaction Mixture Holding | 65 (30° C.)-125 (30° C.) 60 min | 10 mL | The crystallizing mixture became very thick, 400 RPM |
| Cooling down to 0° C. | 125 (30° C.)-170 (0° C.) 45 min | N/A | The crystallizing mixture was very thick but stirrable, 300 RPM |
| Holding at 0° C. | 170 (0° C.)-210 (0° C.) 40 min | N/A | The crystallizing mixture was thick but fluid, 300 RPM |

The precipitated solids were filtered off, washed on filter with cold acetone-water mixture (3:1, 0° C., 2×30 mL) and with acetone (1×40 mL, to get all material dried) and dried on filter till constant weight. The procedure provided ABUK sulfate (11.7 g, 80.5% yield, lot D) with 24 ppm DHC content, as shown in Table 4. The crystallized product ABUK sulfate Lot D exhibited diminished DHC impurity to 24 ppm compared to starting crude ABUK sulfate Lot C with 213 ppm DHC.

TABLE 4

ABUK Sulfate Recrystallization Step Progress by HPLC*.

| Time Event | 14-OH-Codeinone (ABUK) | DHC |
|---|---|---|
| Starting ABUK Sulfate dry (lot C) | 99.37 | 0.0213 |
| Recrystallized ABUK Sulfate dry (lot D) | 99.37 | 0.0024 |
| ABUK Sulfate Mother Liquor | 98.75 | 0.1477 |

*HPLC Normalization Data, %; 15 cm × 4.6 mm Phenomenex NX-C18, 5 μm column)
Mobile phase with pH 8.51 was employed for the DHC analysis.

Example 5

Purification of 14-Hydroxycodeinone Sulfate by Base Formation

Purification of two combined lots of 14-hydroxycodeinone sulfate was performed to eliminate detectable DHC impurity. Two ABUK sulfate lots (lot E, 25.15 g, 170 ppm DHC and lot F; 9.35 g, 161 ppm DHC, totally 34.50 g or 86.6 mmol) were combined, mixed with water (360 mL) and treated with ammonium hydroxide (conc., ~15 mL) at ambient temperature until the mixture was pH 9.0-9.4 (pH indicator paper). Stirring was continued another 0.5 hours and a precipitated ABUK base was filtered off, washed with water (2×50 mL), dried on filter providing the muddy slurry. Semi-dry slurry was treated with hexanes (~300 mL) for 2 hours and filtered off once again, dried on filter providing almost white ABUK base (32.32 g (wet), MW 313.36, lot G).

The ABUK base (Lot G, 32.32 g (wet) was placed in 500-ml Erlenmeyer flask, mixed with 150 ml of water and 7.0 ml of acetic acid till a clear solution formed. $KHSO_4$ (7.06 g) was added over 5 minutes to stirred solution at ambient temperature till a thick stirrable mixture formed. Stirring was continued for 0.5 hours at ambient temperature and then in an ice bath for 50 minutes. Filtering of the precipitated product, rinsing it with icy water (1×20 ml), MEK (methyl ethyl ketone, 2×50 mL) and drying on filter provided ABUK sulfate, 25.01 g, 72% yield (Lot H).

Both lots of starting ABUK sulfate, intermediate ABUK base and product ABUK sulfate were evaluated by HPLC Normalization Data Method, on 15 cm×4.6 mm Phenomenex NX-C18, 5 μm column, and are shown in Table 5. No DHC impurity was detected in the product dry ABUK sulfate by the HPLC normalization method.

TABLE 5

HPLC Data* for ABUK Sulfate Preparation from ABUK Base.

| Time Event | 14-OH-Codeinone (ABUK) | DHC |
|---|---|---|
| ABUK Sulfate Lot E | 99.98 | 0.0170 |
| ABUK Sulfate Lot F | 99.98 | 0.0161 |
| ABUK Base dry Lot G | 99.65 | 0.0202 |
| ABUK Sulfate Lot H | 99.86 | ND |

*HPLC Normalization Data, %; 15 cm × 4.6 mm Phenomenex NX-C18, 5 μm column;
ND = not detected.

Example 6

Purification of Combined Lots of ABUK Base by Formation of ABUK Sulfate

14-Hydroxycodeinone (ABUK) base (combined lot, impure, total weight 17.32 g, 55.27 mmol) was dissolved in the solution of 5 g acetic acid in 60 mL of water at 60° C. Complete dissolution was observed. 70 g of saturated solution of $Na_2SO_4$ was added to the solution of ABUK. Precipitation started after several minutes. The formed slurry was naturally cooled to room temperature during 2 hours. Solids were filtered off, washed with saturated solution $Na_2SO_4$ (1×30 mL), acetone (2×40 mL) and dried on filter to give 14-hydroxycodeinone sulfate as a yellow/white solid (12.95 g, 58.8% yield) Lot I. No DHC impurity was detected in Lot I according to HPLC normalization method.

Example 7

Preparation of ABUK Sulfate from ABUK Base of Mother Liquors

A mixture of ABUK Base Lot J (8.55 g, 27.27 mmol) and ABUK Base lot K, (6.32 g, 20.17 mmol) (totally 47.44 mmol) was made in 250-mL RBF and dissolved in the mixture of water (115 mL and acetic acid (5 mL) at ambient temperature. Sodium sulfate (16.15 g) was added portion-wise over four minutes to the magnetically stirred ABUK acetate solution. Precipitation of the ABUK sulfate as a product occurred in four minutes after end of addition of sodium sulfate. The crystallizing mixture was stirred at ambient temperature for two hours and at 5° C. for 0.5 hours. The precipitated product was filtered off, washed on filter with cold water (2×15 mL) and acetone (2×40 mL) and dried on filter to constant weight 10.05 g, 25.22 mmol, 53% yield of a slightly yellowish crystalline powder (lot L). The starting ABUK base and product were evaluated by HPLC Normalization Data, on 15 cm×4.6 min Phenomenex NX-C18, 5 μm column, and are shown in Table 6. No DHC was detected in the product dry ABUK sulfate Lot L by the HPLC normalization method as shown in Table 6.

TABLE 6

HPLC Data on ABUK Sulfate Preparation from ABUK Base.

| Time Event | 14-OH-Codeinone (ABUK) (%) | DHC (%) |
|---|---|---|
| ABUK Base Lot K | 98.72 | 1.2297 |
| ABUK Base dry Lot J | 98.40 | 0.6843 |
| ABUK Sulfate dry Lot L | 99.65 | ND |

Example 8

Preparation of ABUK Sulfate from ABUK Base with Sulfuric Acid

Mixing of dry impure ABUK base (24.96 g, 79.66 mmol), water (112 mL) and acetic acid (3.51 mL) was performed with stirring for 10 min, followed by addition of sulfuric acid (13.27 g, 30%, 40.63 mmol) over 10 min, and mechanical stirring (thick in the beginning and stirrable after 15 min of stirring at 20° C.). The mixture was stirred for 40 min at ambient temperature, followed by cooling with ice-bath, holding for 40 min, filtering off the product. The product ABUK sulfate was washed with acetone (60 mL, 40 mL), dried on filter. Yield of purified ABUK was 28.24 g, 89% (lot M). Evaluation by HPLC revealed ABUK −99.99%, DHC −0.0053%.

Example 9

Preparation of ABUK Solution in Acetic Acid and its Hydrogenation to Form Oxycodone Acetate Barium diacetate (10.0 g, 39.15 mmol) was dissolved in 10% acetic acid up to 100 mL solution (pH 4.5-5.0). The first crop ABUK sulfate material (27.81 g, 69.80 mmol, containing 34.9 mmol of sulfuric acid) was added portion-wise to the prepared solution over 15 minutes at 5-10° C. with magnetic stirring. Stirring was continued for 45 minutes, Celite (3.0 g) was added to the mixture and precipitated material was filtered off on a vacuum filter with Celite cake. The filtrate was transferred into 3-neck 250-mL RBF, purged with argon, mixed with Pd/C catalyst (0.74 g, 10%, 50% LOD) and hydrogen was introduced into the reaction mixture with a gas dispersion tube at 5° C. at magnetic stirring. Additional Pd/C catalyst (0.84 g) was added after 2 hours of hydrogenation. After 6 hours of hydrogenation, formic acid (97%, 10 mL) was introduced into the reaction mixture. The reaction mixture was warmed gradually from 5 to 15° C. overnight. Reaction progress was followed by HPLC, as shown in Table 7.

The reaction mixture was purged with argon and stirred with Celite (3 g, 15 minutes). Filtering off Pd/C catalyst on filter with Celite cake provided almost colorless (yellow tint) solution containing oxycodone acetate. The reaction progress was followed by HPLC as shown in Table 7.

TABLE 7

Reduction Step Reaction Progress for preparation of Oxycodone acetate.

| Time Event | Oxycodone | 14-OH-Codeinone (ABUK) | DHC | Oxycodol α/β isomers |
|---|---|---|---|---|
| ABUK Acetate in 10% Acetic Acid | NA | 99.88 | ND | NA |
| 1.75 h reduction | 18.67 | 80.88 | ND | ND |
| 3.5 h | 98.74 | 0.1483 | ND | 0.78/ND |
| 5.75 h | 98.88 | 0.1051 | 0.0325 | 0.84/0.05 |
| After night | 98.04 | ND | 0.0306 | 0.88/0.25 |
| Oxycodone acetate (filtrate) | 98.66 | ND | 0.0420 | 0.84/0.28 |

HPLC Data, %; 7.5 cm × 4.6 mm Phenomenex NX-C18, 3 μm column)

Example 10

Preparation of Oxycodone Base as a Dry Solid

Oxycodone acetate solution was diluted with isopropanol (25 mL), cooled to ~10° C. and neutralized at 10° C. to 5° C. with ammonium hydroxide (conc., ~30 mL until pH ~9.5). Stirring continued for 10 minutes and precipitated solids were filtered off, washed on filter with water (20 mL, 2×50 mL, 10 mL) and dried on filter for 0.5 hours. The light gray wet material (22.29 g) was prepared. This material was dissolved in chloroform (150 mL), treated with sodium sulfate (anhydrous) for one hour. Solvent was removed in vacuum and gray powder was dried on rotary evaporator for one hour at 50° C. in the bath, providing oxycodone base (16.31 g, 51.72 mmol, 74.1% yield on ABUK sulfate). Impurity profile is shown in Table 8.

TABLE 8

HPLC Data on Preparation of Oxycodone base from Oxycodone Acetate.

| Time Event | Oxycodone | 14-OH-Codeinone (ABUK) | DHC | Oxycodol α/β isomers |
|---|---|---|---|---|
| Oxycodone acetate (filtrate) | 98.62 | ND | 0.0321 | 0.88/0.33 |
| Oxycodone Base dry | 99.22 | 0.0042 | 0.0280 | 0.45/0.20 |

*HPLC Data, %; 7.5 cm × 4.6 mm Phenomenex NX-C18, 3 μm column.

Example 11

Preparation of Oxycodone HCl from ABUK Sulfate

A mixture of ABUK sulfate (42.40 g, Lot N) and water (130 mL) was made in a 250-mL 3-neck RBF. The mixture was purged with argon, and Pd/C catalyst (2.70 g) was added to stirred mixture at ambient temperature. Reaction progress was monitored by HPLC as shown in Table 9. The reaction completed in two hours. Formic acid (20 mL) was added to the reaction mixture and the mixture was kept at 50-60° C. for 45 minutes and was allowed to cool to ambient temperature overnight.

Pd/C Catalyst was filtered off and ammonium hydroxide was used for the oxycodone base precipitation (~60 mL) at temperature less than 15° C. Precipitated product was washed with water (2×75 mL) and dried on filter giving 28.07 g of oxycodone base. The oxycodone base was transferred into 250-mL RBF with Pd/C catalyst (0.59 g) and water (120 mL). Formic acid (4.36 mL) was added (pH 2.1) and stirring continued for 45 minutes at 50-60° C. The reaction mixture was cooled to ambient temperature, catalyst was filtered off, and oxycodone base was isolated with ammonium hydroxide addition to the filtrate at temperature lower than 20° C. Drying on filter provided 29.51 g of the oxycodone base ($2^{nd}$ crude, Lot O).

The oxycodone base (29.51 g, Lot O) was transferred into a 3-neck 250-mL RBF, dissolved in chloroform (~100 mL). The mixture was heated till the distillation started and IPA (totally 250 mL) was added portion-wise till temperature in vapors was stable at 88° C. (1.5 hours). The mixture was allowed to cool to ambient temperature; solids were filtered, washed on filter with IPA (2×20 mL) and dried on filter to provide purified oxycodone base, Lot P, 26.73 g, 84.76 mmol, yield 95% on oxycodone base crude (28.07 g). The oxycodone base was divided into two portions, and each portion was converted to oxycodone hydrochloride as described.

The first portion of purified Oxycodone base lot P (13.56 g, 43.0 mmol) was dissolved (in 80-mL beaker over 15 minutes) in a mixture of water (13 mL) and acetic acid (3 mL). Hydrochloric acid (10.41 mol/kg, 5.0 g, or 51.6 mmol) was added to the solution over 5 minutes. Stirring was continued for another 40 minutes and IPA (55 mL) was added over 15 minutes. Stirring was continued for another 30 minutes. Precipitated product was filtered off, washed on filter with IPA (2×20 ml) and acetone (2×20 mL), dried on filter providing 14.74 g oxycodone HCl (39.86 mmol, 93% yield on OC base purified) lot Q.

The second portion of purified oxycodone base lot P (13.00 g, 41.22 mmol) was dissolved (in 80-mL beaker over 10 minutes) in a mixture of water (17 mL) and acetic acid (2.80 mL). Ammonium chloride (MW 53.49, 2.20 g or 41.22 mmol) was added to the stirred solution over 20 minutes. Stirring was continued for another two hours at ambient temperature and then the crystallizing solution was cooled down to +5° C. (ice bath). Stirring was continued for one hour and precipitated product was filtered off, washed with cold ethanol (2×7 mL), IPA (15 mL) and acetone (20 mL). Drying on filter provided 10.88 g of oxycodone HCl, Lot R (29.42 mmol, 71% yield on oxycodone base purified).

TABLE 9

HPLC Data on Reduction and Oxycodone (OC) HCl Preparation.

| Time Event | Oxycodone | 14-OH-Codeinone (ABUK) | DHC | Oxycodol |
|---|---|---|---|---|
| ABUK sulfate (lot N) | NA | 99.99 | 0.0067 | NA |
| 2 hours of hydrogenation | 98.29 | 0.0247 | 0.0289 | 1.50/0.09 |
| After 50° C. Heat and Cool | 98.20 | 0.0440 | ND | 1.53/0.16 |
| After formic acid $2^{nd}$ Reduction (reaction mixture) | 98.85 | 0.0765 | 0.0102 | 0.53/0.14 |
| OC base 2 (isolated, Lot O) | 99.03 | ND | ND | 0.45/0.20 |
| OC base isolated, IPA purified, Lot P [(1)] | 99.57 | 0.0022 | 0.0057 | 0.23/0.18 |
| OC HCl crystalline Lot Q | 99.96 | ND | ND | 0.0166/ND |
| OC HCl crystalline Lot R | 99.99 | ND | ND | 0.0130 |

Note:
Area normalization method HPLC Data, %; 15 cm × 4.6 mm Phenomenex NX-C18, 5 μm column)

The following HPLC methods were employed for ABUK determination in Lot Q and Lot R Oxycodone HCl Samples (R&D Assay method). A 1 ml/min flow rate was employed.

1. Averaged response of 8.24 μg/ml external standard (pure oxycodone base solution in 0.85% phosphoric acid, two 10 μl-injections):

(717.0+731.3)/2=724.15.

2. Sample preparation was performed by dissolution of 76.3 mg of Lot Q sample in 2.25 g of 0.85% phosphoric acid for a sample concentration 76.3 mg/2.25 mL=33.91 mg/ml or 0.03391 g/ml. Sample preparation was performed by dissolution of 65.3 mg of Lot R sample in 2.02 g of 0.85% phosphoric acid) for a sample concentration 65.3 mg/2.02 mL=32.33 mg/ml or 0.03233 g/ml.

3. The Response of 50 mkl Lot Q sample injection: 48.3; and response of 50 μl Lot R sample injection: 21.8

4. Calculation of ABUK content was calculated as follows: ppm=Rsmpl/Rstd×Cstd (mkg/ml)/Csmpl (g/mL)×1/1.715× 1/5×0.85; where 1/5 is adjusting factor for injection volumes; 0.85 is adjusting factor of oxycodone base and oxycodone HCl hydrate according to their molecular weights (315.36/369.84=0.85); 1/1.715 is adjusting factor for RRF (relative response factor, ABUK has conjugated double bonds and its absorbance is higher than absorbance of oxycodone, DHC or oxycodol).

The amount of Sample Lot Q ABUK content was determined as =48.3/724.15×8.24/0.03391×1/1.715×1/5× 0.85=1.61 ppm. Indirect ABUK determination (oxycodol as a reference) gave 1.73 ppm number: (48.3 (ABUK area)/ 2700.9(oxycodol area)=0.0178; and 0.0178*0.0166%/1.71 (RRF)=1.73 ppm.

The amount of Sample Lot R ABUK content was determined as =21.8/724.15×8.24/0.03233×1/1.715×1/5× 0.85=0.76 ppm. Indirect ABUK determination (oxycodol as a reference) gave 0.87 ppm number: (21.8 (ABUK area)/1903 (oxycodol area)=0.01146; 0.01146*0.0130%/1.71 (RRF)=0.87 ppm.

Therefore, methods are provided for preparation of oxycodone hydrochloride from 14-hydroxycodeinone sulfate that provide oxycodone hydrochloride with less than 10 ppm, less than 5 ppm, less than 2 ppm, or less than 1 ppm, of 14-hydroxycodeinone (ABUK) in the final product.

Example 12

Oxycodone HCl Preparation and Crystallization

Purified oxycodone base (19.22 g, 60.95 mmol, Lot S) and a mixture of water (28.83 g) and acetic acid (2.82 g, 16.19 mmol/g, 44.70 mmol) were charged into 150-mL RBF, equipped with mechanical stirrer. Stirring of the mixture at ambient temperature (230 RPM) resulted in a thin suspension formation. Hydrochloric acid (6.94 g, 10.094 mmol/g, 70.09 mmol) was added portion-wise over 45 minutes: at the beginning—about 2.30 g (over ~4 minutes, the mixture became transparent, followed by a precipitation); the rest of the hydrochloric acid was added portion-wise (5 drops at once) over 40 minutes (rate of stirring was increase to 250 RPM after 30 minutes). The mixture was stirred for 0.5 hours at ambient temperature, 0.5 hours at ice-bath temperature, and cold IPA (0° C., 77 mL) was added over 25 minutes. Stirring continued for 0.5 hours, and the precipitated product was filtered off. It was washed with IPA (2×40 mL) and acetone (2×40 mL), dried on filter providing 21.73 g (58.76 mmol, 96.4% yield) of oxycodone HCl crystalline white solids, Lot T. Impurity profiles of materials of interest were monitored by HPLC, normalization method, as shown in Table 10.

TABLE 10

HPLC* Profile of Oxycodone (OC) base, OC HCl and its Mother Liquor (ML).

| Sample | DHC | Oxycodol α/β isomers | ABUK | Oxycodone |
|---|---|---|---|---|
| OC Purified Lot S | 0.0320 (pH 8.5) | 0.10/ND | 0.0023 | 99.73 |
| OC HCl Lot T | ND (pH 8.5) | ND/ND | ND (6 ppm, QC Assay method) | 99.79 |
| OC HCl Lot T -ML | 0.2155 (pH 8.5) | 0.6535/ND | ND | 98.66 |

*normalization method, %, HPLC Mobile Phase pH 9.50, except DHC determination, ML = mother liquor As shown in Table 10, this method for conversion of oxycodone base to oxycodone hydrochloride does not promote acid catalyzed dehydration of DHC impurity to 14-hydroxycodeinone (ABUK); but rather the DHC remains in the mother liquor. In addition, this method provides oxycodone hydrochloride with not more than 10 ppm 14-hydroxycodeinone.

Therefore, by a method comprising at least partially dissolving oxycodone base in acetic acid and water and converting to oxycodone hydrochloride with hydrochloric acid at ambient temperature, oxycodone hydrochloride was provided without detectable 14-hydroxycodeinone (ABUK) by the HPLC normalization method, and with not more than 10 ppm 14-hydroxycodeinone level by QC Assay method.

Example 13

Preparation of Oxycodone HCl from 14-Hydroxycodeinone Sulfate

Figure 5:
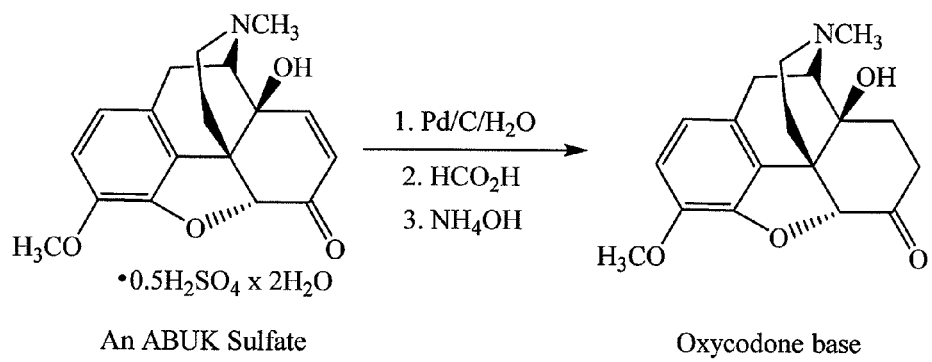
FIG. 5 shows a synthetic route for preparation of oxycodone base from reduction of 14-hydroxycodeinone sulfate with formic acid over Pd/C-catalyst.

Oxycodone hydrochloride was prepared from 14-hydroxycodeinone sulfate as shown in FIG. 5. A mixture of ABUK hemisulfate dihydrate (20.0 g, Lot U lot, 50.20 mmol) and water (65 mL) was made in a 250-mL 3-neck RBF. This mixture was purged with argon and Pd/C catalyst (0.65 g, 10%, 50% LOD) was loaded into the flask. Hydrogen gas purged into the flask at ambient temperature for 5.25 hours and HPLC analysis indicated almost the end of reaction. Formic acid (5 mL) and a fresh portion of Pd/C catalyst (0.37 g) were added to the reaction mixture and the reaction mixture was heated at 50° to 60° C. for 45 minutes and cooled naturally till ambient temperature.

Pd/C catalyst was filtered off on filter with Celite cake, flask and cake were rinsed with acetic acid (5%, 15 mL) and water (2×20 mL). Oxycodone base was isolated using ammonium hydroxide (conc., ~35 mL) by neutralization of the acids in the filtrate till pH ~9.5 at 5-10° C. Oxycodone base was washed with water (3×40 mL) and dried on filter providing 12.57 g of dry oxycodone base crude, Lot V. This amount of oxycodone base crude was dissolved in chloroform (~50 mL, 250-ml 3-neck RBF), this solution was heated to boiling point and IPA (250 mL) was added gradually over 1 hour at boiling point of the mixture and then 150 mL of the solvent was distilled (at 58-82° C.). The mixture was cooled down gradually to ambient temperature, the precipitated oxycodone base was filtered off, washed with IPA (cold, 2×15 mL) and dried on filter providing 11.92 g (37.80 mmol) of purified oxycodone base, Lot W (95% yield). Total yield on ABUK sulfate was 75%. Impurity profile is shown in Table 11.

TABLE 11

HPLC Data on ABUK Reduction and Oxycodone Base Preparation.

| Time Event | Oxy-codone | 14-OH-Codeinone (ABUK) | DHC | Oxycodol α/β isomers |
|---|---|---|---|---|
| ABUK (lot U) | NA | 99.99 | 0.0063 | NA |
| 5.25 hours hydrogenation | 95.52 | 0.0279 | 0.0210 | 1.38/0.08 |
| After hydrogenation at 50° with FA | 95.31 | 0.0185 | 0.0065 | 1.45/0.27 |
| OC Filtrate as Formate-Acetate Salts | 95.17 | 0.0024 | 0.0119 | 1.50/0.30 |
| OC Base Crude, lot V | 98.31 | ND | 0.0085 | 0.66/0.16 |
| OC Base IPA treated, Lot W | 99.77 | 0.0119 | 0.0109 | 0.04/0.03 |

FA—Formic Acid, HPLC Data, %; 15 cm×4.6 mm Phenomenex NX-C18, 5 μm column.

Example 14

Reduction of ABUK Sulfate with Formic Acid Over Pd/C Catalyst

ABUK sulfate (12.03 g, 30.19 mmol, Lot X) was slurried in 48 mL of water (initial pH was 2.61). Pd/C catalyst (0.3 g, 10%, 50% LOD) was added to the slurry, then 0.2 ml of formic acid was added to the slurry to adjust to pH 1.34. Reaction was monitored according to pH of the reaction mixture, time and amount of added formic acid as shown in Table 12.

TABLE 12

Reduction of ABUK Sulfate with Formic Acid (FA).

| Time, h | pH before FA addition | Comments | pH after FA addition |
|---|---|---|---|
| 0.00 | 2.61 | 0.2 mL formic acid added to reaction mixture | 1.34 |
| 0.50 | 4.23 | 0.2 mL formic acid added to reaction mixture | |

TABLE 12-continued

Reduction of ABUK Sulfate with Formic Acid (FA).

| Time, h | pH before FA addition | Comments | pH after FA addition |
|---|---|---|---|
| 1.00 | 4.44 | 0.3 mL formic acid added to reaction mixture | 1.32 |
| 1.75 | 4.75 | 0.5 mL formic acid added to reaction mixture | 1.32 |
| 4.00 h | 2.32 | 0.2 mL formic acid added to reaction mixture | 1.64 |
| 4.50 h | NA | Reaction was stopped | NA |

The catalyst was filtered off, washed with water (2×10 mL), pH of the filtrate was adjusted to 9, using ammonium hydroxide conc. aqueous solution. After one hour stirring, the product was filtered off, washed with water (2×20 mL) and dried on the filter to constant weight to give oxycodone free base as white powder −8.8 g. (92.4% yield), lot Y.

Example 15

Oxycodone Hydrochloride Preparation and Crystallization

As described above, oxycodone base purified (Lot P, 13.56 g, 43.0 mmol) was dissolved (in 80-mL beaker over 15 minutes) in the mixture of water (13 mL) and acetic acid (3.0 mL) at ambient temperature. Hydrochloric acid (10.41 mol/kg, 5.0 g or 51.6 mmol) was added to the solution over 5 minutes. Stirring was continued for another 40 minutes and IPA (55 mL) was added over 15 minutes. Stirring was continued for another 30 minutes. Precipitated product was filtered off, washed on filter with IPA (2×20 ml) and acetone (2×20 mL), dried on filter providing 14.74 g oxycodone HCl (39.86 mmol or 93% yield on OC base purified)—lot Q.

The HPLC profile of the final product oxycodone hydrochloride, Lot Q, and the starting material, oxycodone base, Lot P, are shown in Table 13. Two special oxycodone hydrochloride Lot Q HPLC analyses were performed using R&D and QC Assay methods. Oxycodone HCl Lot Q exhibited 14-hydroxycodeinone impurity by HPLC R&D laboratory method of 1.61 ppm, and QC laboratory method of 3.0 ppm.

TABLE 13

HPLC Normalization Analysis of Lot Q Oxycodone HCl and Its Precursor.

| Time Event | Oxycodone | 14-OH-Codeinone (ABUK) | DHC | Oxycodol α/β isomers |
|---|---|---|---|---|
| OC base isolated IPA purified Lot P | 99.57 | 0.0022 | 0.0057 | 0.23/0.18 |
| OC HCl crystalline, Lot Q | 99.96 | ND | ND | 0.0166/ND |

Example 16

Evaluation of Oxycodone Hydrochloride with Improved Impurity Profile

Oxycodone hydrochloride was prepared from oxycodone base purified by (a) dissolution of oxycodone as its acetate salt in water, by (b) conversion of the oxycodone acetate salt into its hydrochloric acid salt at ambient temperature by using either hydrochloric acid or ammonium chloride, as indicated, and by (c) crystallization of oxycodone hydrochloride as provided herein, as noted in Table 14. As used herein "PF" is used to denote purification factor (in parenthesis) which refers to ratio of impurity content before and after preparation, purification and/or crystallization. "ND" refers to not detected. "NA" means not applicable.

TABLE 14

Impurity Profile for Conversion of Oxycodone Base to Oxycodone Hydrochloride by Acetic Acid Method or by Ammonium Chloride Method.

| Substance | OC, % | ABUK, ppm (PF) | DHC, ppm (PF) | Oxycodol (major isomer), % (PF) | HPLC Method, Notes |
|---|---|---|---|---|---|
| OC Base Crude Lot Z | 98.31 | ND | 85 | 0.6600 | Normalization |
| OC Base IPA Purified Lot AA (IPA + chloroform) | 99.70 | 119 | 109 | 0.0400 | Normalization |
| OC HCl Lot BB (HCl method) | NA | 6.10 (19.51) | 3.84 (28.39) | 0.0103 (3.88) | R&D, Assay Method |
| | NA | 2 (59.5) | NA | NA | QC, Assay Method |
| OC Base Crude Lot CC | 98.55 | ND | 47 | 1.0400 | Normalization |
| OC Base IPA Purified Lot DD (IPA + chloroform + MeOH) | 99.86 | ND | 89 | 0.0800 | Normalization |
| OC HCl Lot EE (ammonium chloride method) | 99.96 | ND | ND | 0.0037 (2.16) | Normalization |
| | NA | 0.27 | 2.64 (33.71) | 0.0165 (4.85) | R&D, Assay Method |
| | NA | 2 | NA | NA | QC, Assay Method |
| OC Base Crude Lot O | 99.03 | ND | ND | 0.4500 | Normalization |
| OC Base IPA Purified Lot P (IPA + chloroform) | 99.57 | 22 | 57 | 0.2390 | Normalization |
| OC HCl Lot Q | NA | 1.61 (13.66) | 6.53 (8.73) | 0.0090 (26.56) | R&D, Assay Method |
| | NA | 3 (7.33) | NA | NA | QC, Assay Method |
| OC HCl Lot R (ammonium chloride method) | NA | 0.76 (28.95) | 2.33 (24.46) | 0.0066 (36.21) | R&D, Assay Method |
| | NA | 4 (5.5) | NA | NA | QC, Assay Method |

Each of the oxycodone hydrochloride samples in Table 14 exhibits an Impurity Profile for oxycodone hydrochloride samples with not more than 10 ppm, or not more than 5 ppm, or not more than 3 ppm, or not more than 2 ppm, or not more than 1 ppm 14-hydroxycodeinone.

Each of the oxycodone hydrochloride samples in Table 14 exhibits an Impurity Profile for oxycodone hydrochloride samples with not more than 0.02%, 0.015%, or 0.01% 6-oxycodol, major isomer.

Each of the oxycodone hydrochloride samples in Table 14 exhibits an Impurity Profile for oxycodone hydrochloride samples with not more than 10 ppm, or not more than 5 ppm DHC.

In case of oxycodone hydrochloride sample Lot BB, as a result of oxycodone hydrochloride preparation and its crystallization at ambient temperature, ABUK impurity was present at only 6.10 ppm, (R&D HPLC assay method). Oxycodone hydrochloride sample Lot BB impurity oxycodol major isomer was present at 0.0103%, and DHC was present at 3.84 ppm (R&D HPLC assay method).

In case of oxycodone hydrochloride Lot EE, prepared via the ammonium hydrochloride method and crystallization at ambient temperature, ABUK was present at only 0.27 ppm (R&D HPLC assay method). Lot EE oxycodone hydrochloride also exhibited a reduced impurity profile for DHC and oxycodol impurities with 2.64 ppm DHC impurity, and 0.0165% oxycodol, major isomer (R&D HPLC assay method).

In case of Lot Q oxycodone hydrochloride sample, as a result of oxycodone hydrochloride preparation with hydrochloric acid and crystallization at ambient temperature, ABUK was present at only 1.61 ppm (R&D HPLC assay method). Lot Q oxycodone hydrochloride also exhibited 6.53 ppm DHC, and 0.009% oxycodol (R&D HPLC assay method).

In case of Lot R oxycodone hydrochloride prepared by ammonium chloride method, and as a result of oxycodone hydrochloride preparation and crystallization at ambient temperature, ABUK was present at only 0.76 ppm (R&D HPLC assay method). Lot R Oxycodone hydrochloride Lot R also had minimal DHC and oxycodol impurities of DHC 2.33 ppm, and 0.0066% oxycodol (R&D HPLC assay method).

Example 17

Oxycodone Crude Purification

Oxycodone base crude Lot FF (21.76 g) was charged into 250-mL one-neck RBF with propylene glycol (38 mL), water (76 mL) and IPA (25 mL) mixture. The mixture was heated at reflux for 2 hours (115-133° C. in the bath), cooled down to ambient temperature over 30 minutes and kept in the ice bath for 0.5 hours. The precipitated product was filtered off, washed with water twice (30 and 15 mL) and dried on filter till constant weight (20.96 g or 96.3% yield, Lot GG). Starting material and product was evaluated by HPLC as shown in Table 15. Data, %; 15 cm×4.6 mm Phenomenex NX-C18, 5 µm column). Purification of crude oxycodone base by use of propylene glycol and IPA significantly reduced DHC and oxycodol impurities in the purified oxycodone base.

TABLE 15

HPLC Data on Oxycodone Base Purification.

| Time Event | Oxycodone | 14-OH-Codeinone (ABUK) | DHC | Oxycodol α/β isomers |
|---|---|---|---|---|
| OC Crude, Lot FF | 97.85 | ND | 0.0482 | 0.98/0.36 |
| OC Base Purified, Lot GG | 99.48 | ND | 0.0129 | 0.31/0.14 |

(HPLC Data, %; 15 cm × 4.6 mm Phenomenex NX-C18, 5 µm column)

Example 18

Oxycodone Crude Purification

Oxycodone base crude (31.23 g, Lot FF) was charged into 500-mL one-neck RBF with IPA (20 mL), water (114 mL) and methoxyethanol (57 mL) mixture. The mixture was heated at reflux for 4.5 hours (110-115° in the bath), cooled down to ambient temperature over 30 minutes and kept in the ice bath for 0.5 hours. The precipitated product was filtered off, washed with water (50 mL and 30 mL) and dried on filter till constant weight (29.83 g or 95.5% yield, Lot II). Impurity profiles are shown in Table 16.

TABLE 16

HPLC Data on Oxycodone Base Purification.

| Time Event | Oxycodone | 14-OH-Codeinone (ABUK) | DHC | Oxycodol α/β isomers |
|---|---|---|---|---|
| OC Crude, Lot FF | 97.95 | ND | 0.0482 | 0.98/0.36 |
| OC Base, Lot II | 99.65 | 0.0062 | 0.0133 | 0.25/0.12 |

The methods provided herein for oxycodone hydrochloride preparation and crystallization at ambient temperature using aqueous acetic acid as a media for the oxycodone hydrochloride preparation, or generation of oxycodone acetate prior to introduction of HCl or ammonium chloride, and various crystallization techniques are employed to minimize DHC, ABUK and oxycodol impurity content in the final finished product.

Example 19

14-Hydroxycodeinone Sulfate Preparation and Crystallization

In this experiment, thebaine is converted to ABUK sulfate and crystallized with product washing on filter with 40% ammonium sulfate aqueous solution (($NH_4$)$_2SO_4$) in order to prevent product losses due to its high solubility in water or aqueous organic solvents, such as acetone/water mixtures.

A 250 mL jacketed reactor was subsequently charged with thebaine (lot TCPS-132, Lot LL, 79% Assay Thebaine –37.97 g, MW 311.37 g/mol; 96.35 mmol, 1 equivalent), solution of DI water (8.03 g) and 97% formic acid (5.72 g, 120.54 mmol, 1.25 equiv) and then sodium hydrogen sulfate (13.57 g, 98.28 mmol, 1.02 equiv. to thebaine). The mixture was stirred (125 RPM) at 20° C. for 5 minutes to give a good stirrable mixture. Hydrogen peroxide (30%, 13.64 g, 1.25 equiv. to thebaine) was added to the stirred reaction mixture at 20° C. over two minutes. After all additions were completed, the temperature of the reaction mixture was 30° C. The reaction temperature (70° C.) was reached after 8 minutes of heating with Julabo (set to 72° C.). Stirring was continued for 110 minutes until the complete thebaine conversion into 14-hydroxycodeinone. Complete dissolution and a clear reaction mixture were observed after 7 minutes of heating at 70° C. The precipitation of yellow solids occurred after 50 minutes of stirring at 70° C. (after seeding by scratching the flask wall). The reaction mixture was cooled down to 25° C. over a period of 52 minutes. Water (50 mL) was added to the crystallizing mixture in two portions: 50 mL at 30° C. (stirrer was set for 250 RPM) and another 50 mL portion at 25° C. Stirring at 25° C. was continued for 30 minutes until additional product crystallization occurred. The crystallizing mixture was cooled down to 0° C. and kept at 0° C. for 30 minutes. See cooling crystallization profile in Table 17. The precipitated product was filtered off, washed on filter with cold 40% ammonium sulfate aqueous solution. Drying on filter provided 30.08 g of yellow powder of ABUK sulfate (ABUK×0.5$H_2SO_4$×2$H_2O$, MW 398.42, 75.50 mmol or 78.4% yield, lot MM).

TABLE 17

Time-Temperature Cooling Profile for Crystallization of 14-hydroxycodeinone sulfate.

| Event | Current Time, minutes, (temperature), operation time (min) | Added Water, mL | Notes, Stirrer RPM |
|---|---|---|---|
| End of Reaction | 0.00 (70° C.) | 0.0 | The crystallizing mixture is fluid, 125 RPM |
| Cooling and stirring | 0.0 (70° C.)- 52 (25° C.) 52 min | 50 mL at 30° C. and 50 mL at 25° C. | The crystallizing mixture is fluid, 125 RPM and 250 RPM after water addition |
| 25° C. Reaction Mixture Stirring | 52 (30° C.)- 82 (30° C.) 30 min | NA | The crystallizing mixture is fluid, 250 RPM |
| 25° C. to 0° C. Reaction Mixture Cooling | 82 (25° C.)- 127 (0° C.) 45 min | NA | The crystallizing mixture is fluid, 250 RPM |
| Stirring at 0 C | 127 (0° C.)- 157 (0° C.) 30 min | NA | The crystallizing mixture is fluid, 250 RPM |

Example 20

Oxycodone Base Preparation to Minimize Oxycodol Formation

ABUK sulfate (30.03 g or 75.50 mmol, lot MM, 020-140-149) and water (135 mL) were charged into 3-neck 500-mL RBF. The mixture was stirred magnetically with argon gas purging for about 10 minutes (gas-dispersion tube, moderate gas flow, magnetic stirrer) at around 40° C. Pd/C catalyst (0.90 g, 10% Pd/C, LOD 50%) was mixed with water (20 mL) and transferred into the flask. Hydrogen gas was introduced into the heterogeneous mixture in the flask at 38-42° C. for 140 minutes. The reaction mixture was cooled down to ambient temperature, catalyst was filtered off and washed with water (~3×30 mL). Oxycodone crude base was isolated by precipitation with concentrated aqueous solution of ammonium hydroxide (~9 mL) until pH ~9.2-9.5 at 20-22° C. (mechanical stirring, 250 RPM). The precipitate was washed with water (1×50 mL, 1×25 mL) and dried on filter till constant weight. The procedure provided oxycodone base crude: 19.74 g (62.60 mmol or 82.9% yield on ABUK sulfate; lot NN).

In this experiment, ABUK sulfate is reduced to oxycodone base crude product in an aqueous system at 38-42° C. without acetic acid. The method preserved optimal activity of Pd/C catalyst and a high rate of reduction was accompanied by a somewhat lower oxycodol by-product formation (1.16% in the reaction mixture instead 1.25-1.60% with acetic acid co-solvent), as shown in Table 18.

TABLE 18

HPLC Data on ABUK Sulfate Reduction and Oxycodone Base Preparation

| Time Event | Oxycodone | 14-OH-Codeinone (ABUK) | DHC | Oxycodol α/β isomers |
|---|---|---|---|---|
| 60 min hydrogenation | 38.32 | 60.48 | ND | 0.82/ND |
| 120 min hydrogenation | 98.59 | ND | ND | 1.41/ND |
| filtrate | 97.57 | 19 ppm | 0.0574 | 1.16/0.13 |
| OC base Crude, Lot NN | 98.29 | 34 ppm | 0.0553 | 0.67/0.05 |

(HPLC Data, %; 15 cm × 4.6 mm Phenomenex NX-C18, 5 μm column)

We claim:

1. A method for preparation of 14-hydroxycodeinone sulfate or a hydrate thereof comprising
   exposing thebaine to hydrogen peroxide or peroxyacid and formic acid in the presence of sodium hydrogen sulfate, sodium sulfate, potassium sulfate, potassium hydrogen sulfate and/or sulfuric acid in an aqueous reaction mixture; and
   isolating a precipitate of 14-hydroxycodeinone sulfate or a hydrate thereof from the reaction mixture.

2. The method of claim 1, wherein the 14-hydroxycodeinone sulfate has less than 0.05%, 0.025%, or 0.01% of a 8,14-dihydroxy-7,8-dihydrocodeinone (DHC) impurity.

3. The method of claim 1, further comprising purifying the 14-hydroxycodeinone sulfate or hydrate thereof.

4. The method of claim 3, wherein the purifying comprises recrystallization of the 14-hydroxycodeinone sulfate or hydrate thereof from an aqueous solvent.

5. The method of claim 4 wherein the recrystallized 14-hydroxycodeinone sulfate is selected from 14-hydroxycodeinone hemisulfate, 14-hydroxycodeinone hemisulfate monohydrate, 14-hydroxycodeinone hemisulfate dihydrate, 14-hydroxycodeinone sulfate sesquihydrate, 14-hydroxycodeinone sulfate dihydrate, 14-hydroxycodeinone sulfate monohydrate, 14-hydroxycodeinone sulfate dihydrate, or 14-hydroxycodeinone monosulfate.

6. The method of claim 1 wherein the exposing step is performed in the presence of sodium hydrogen sulfate, sodium sulfate, potassium sulfate, or potassium hydrogen sulfate.

7. The method of claim 1, wherein the isolated 14-hydroxycodeinone sulfate or hydrate thereof is a 14-hydroxycodeinone hemisulfate or a hydrate thereof.

8. The method of claim 1, wherein the isolated 14-hydroxycodeinone sulfate or hydrate thereof is selected from a 14-hydroxycodeinone sulfate hemihydrate, monohydrate, sesquihydrate or dihydrate.

9. The method of claim 1, wherein the isolated 14-hydroxycodeinone sulfate or hydrate thereof exhibits not more than 0.05% total 8,14-dihydroxy-7,8-dihydrocodeinone (DHC) impurity.

10. The method of claim 9, wherein the isolated 14-hydroxycodeinone sulfate or hydrate thereof exhibits less than 0.01% of an 8,14-dihydroxy-7,8-dihydrocodeinone (DHC) impurity.

* * * * *